United States Patent
Webster et al.

(10) Patent No.: US 12,090,209 B2
(45) Date of Patent:

Twin G^C bases with KRSR (TB-KRSR)

TWIN BASE LINKERS FOR VIRUS INACTIVATION

CROSS-REFERENCE TO RELATED APPLICATIONS

This application claims priority to U.S. Provisional Application No. 63/010,642, filed 15 Apr. 2020, which is incorporated by reference herein in its entirety.

BACKGROUND

Twin base linkers (TBLs) are biocompatible, biodegradable polymers capable of self-assembly to form rosette nanotubes (RNTs) under physiological conditions. TBLs have been suggested for use in drug delivery due to the presence of a hollow core in RNTs that can accommodate drugs, including hydrophobic drugs (Song, et al. (2011)). TBLs contain covalently linked pairs of guanine-like and cytosine-like bases. Six such pairs form a six-member twin rosette stabilized by 36 hydrogen bonds, and the rosettes stack to form RNTs due to dispersion forces, base stacking interactions, and hydrophobic bonding (Fenniri, et al., 2001). The outer surface of RNTs is hydrophilic, rendering them water soluble. RNTs have been shown to bind to cells, to enhance cell growth, and to have other beneficial actions on cells and tissues.

SUMMARY

The present technology provides targeted twin base linkers (TBLs) to bind to and deactivate viruses by preventing their entry into cells. TBLs are formed from two linked nucleic acid bases and have guanine- and cytosine-like hydrogen bond pairing capability. Monomeric units of TBLs are capable of self-assembly to form supramolecular structures such as hollow nanotubules and other structures.

Functionalization of TBLs in the present technology allows them to specifically bind to surface proteins of viruses, where they form structures that can attach to viruses, limit virus entry into cells, and prevent viruses from replicating.

The technology is further summarized by the following listing of features.

1. An antiviral composition comprising a plurality of functionalized twin base linker (TBL) molecules having the general structure

[Peptide]—Linker—[Twin Bases]   or

[Peptide]—Linker—[Twin Bases]
    |
    [Targeting Moiety]   or

[Peptide]—Linker—[Twin Bases]
    |
    [Targeting Moiety] [Targeting Moiety] [Targeting Moiety];

wherein the twin bases comprise a structure according to Formula 1

Formula 1

[chemical structure showing twin base linker with two pyrimidine-like ring systems connected through a linker L containing ethylene groups attached to a central nitrogen]

wherein L is the linker and comprises carbon, nitrogen, and/or oxygen atoms and has a chain length from about 4 to about 20 atoms;
    wherein the peptide moiety contains from about 2 to about 20 L- and/or D-amino acids; and
    wherein optionally one or more targeting moieties are covalently linked to the peptide, the targeting moieties capable of specifically binding a surface-accessible protein of a virus, thereby deactivating the virus, or wherein the targeting moieties are absent, and the peptide moiety is capable of specifically binding a surface-accessible protein of a virus, thereby deactivating the virus.

2. The antiviral composition of feature 1, wherein the targeting moieties are present and are selected from the group consisting of antibodies, aptamers, and peptides.

3. The antiviral composition of feature 1 or feature 2, wherein the peptide comprises one or more amino acids that are positively charged at pH 7 and/or one or more amino acids that are negatively charged at pH 7.

4. The antiviral composition of any of the preceding features, wherein the functionalized TBL molecules comprise one or more targeting moieties covalently attached to the peptide moiety, and wherein the one or more targeting moieties are peptides, each peptide having an amino acid sequence that is distinct from that of the peptide moiety.

5. The antiviral composition of any of the preceding features, wherein the functionalized TBL molecules comprise a peptide moiety or a targeting moiety that binds to a virus spike protein, a virus envelope protein, or both.

6. The antiviral composition of feature 5, wherein the peptide moiety or a targeting moiety comprise a peptide selected from the group consisting of SADE (SEQ ID NO:2), SASD (SEQ ID NO:7), SASE (SEQ ID NO:8), and SACD (SEQ ID NO:9).

7. The antiviral composition of any of the preceding features, comprising functionalized TBL molecules in monomeric form.

8. The antiviral composition of any of the preceding features, comprising functionalized TBL molecules in form of a supramolecular assembly.

9. The antiviral composition of any of the preceding features, wherein the peptide moiety or the targeting moieties bind to a protein of SARS-CoV-2 virus.

10. The antiviral composition of feature 9, wherein the peptide moiety or the targeting moieties bind to S protein of SARS-CoV-2 virus.

11. The antiviral composition of feature 10, wherein the peptide moiety or the targeting moieties also bind to E protein of SARS-CoV-2 virus.

12. The antiviral composition of any of the preceding features, wherein the functionalized TBL molecules, or a supramolecular assembly comprising the functionalized TBL molecules, is capable of inhibiting entry of the virus into a mammalian cell.
13. The antiviral composition of any of the preceding features, wherein the functionalized TBL molecules, or a supramolecular assembly comprising the functionalized TBL molecules, is capable of inhibiting death of mammalian cells infected by the virus.
14. The antiviral composition of any of the preceding features, wherein the composition is for use in treating or preventing a viral infection.
15. The antiviral composition of feature 14, wherein the viral infection is caused by a virus selected from the group consisting of a corona virus, SARS-CoV-2, influenza A virus, influenza B virus, an ebola virus, HIV, an adenovirus, a rhinovirus, hepatitis B virus, hepatitis C virus, MERS virus, measles virus, mumps virus, and chickenpox virus.
16. The antiviral composition of feature 14, wherein the composition is for use in treating or preventing two or more viral infections selected from the group consisting of a corona virus, SARS-CoV-2, influenza A virus, influenza B virus, an ebola virus, HIV, an adenovirus, a rhinovirus, hepatitis B virus, hepatitis C virus, MERS virus, measles virus, mumps virus, and chickenpox virus.
17. The antiviral composition of feature 16, wherein the composition is for treating or preventing infection by SARS CoV-2, influenza A virus, influenza B virus, and rhinovirus.
18. A method to aid in treating or preventing a viral infection, the method comprising administering the antiviral composition of any of the preceding features to a subject in need thereof.
19. The method of feature 18, wherein the viral infection is caused by a virus selected from the group consisting of a corona virus, SARS-CoV-2, influenza A virus, influenza B virus, an ebola virus, HIV, adenovirus, a rhinovirus, hepatitis B virus, hepatitis C virus, MERS virus, measles virus, mumps virus, and chickenpox virus.
20. The method of feature 19, wherein the virus is SARS-CoV-2.
21. The method of any of features 18-20, wherein cellular entry of a virus, virus replication, and/or one or more symptoms of the viral infection are reduced or prevented in the subject.

As used herein, the term "about" refers to a range of within plus or minus 10%, 5%, 1%, or 0.5% of the stated value.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expression "consisting of" or "consisting essentially of".

DETAILED DESCRIPTION

The present technology makes use of targeted twin base linkers (TBLs) to bind to and deactivate viruses. TBLs are capable of self-assembly to form supramolecular nanotubules. Such nanomaterials can attach to viruses, limit virus entry into cells, and prevent viruses from replicating.

Viruses are nanoscale structures and, according to the present technology, viruses can be deactivated by the binding of certain other nanoscale structures, including the macromolecular complexes known as twin base linkers. In the present technology, virus entry into target cells is blocked using a nanomaterial that binds to a structure of the virus involved in cellular entry. The entry and infection of a cell by a virus is a multi-step process, the first step of which is the attachment of the virus to receptor molecules at the surface of the target cell. Although nanomaterials can deactivate many viruses, such as those infecting mammalian cells, including human cells, SARS-CoV-2 is discussed below as an example. The technology can be applied to any virus that infects mammalian cells.

Coronaviruses, including the SARS-CoV-2 virus which causes COVID 19, contain round shells of protein molecules that protect the RNA genetic material. Surrounding the shell is a lipid bilayer membrane containing "spike" proteins (S) that contain the site for binding the cellular receptor on the target cell (see, e.g., R. Al-Attabi, et al., 2019). TBL-derived nanomaterials can be targeted to the S protein so that the nanomaterials bind to the region of the virus that is active in promoting cellular entry.

Figure 1A:
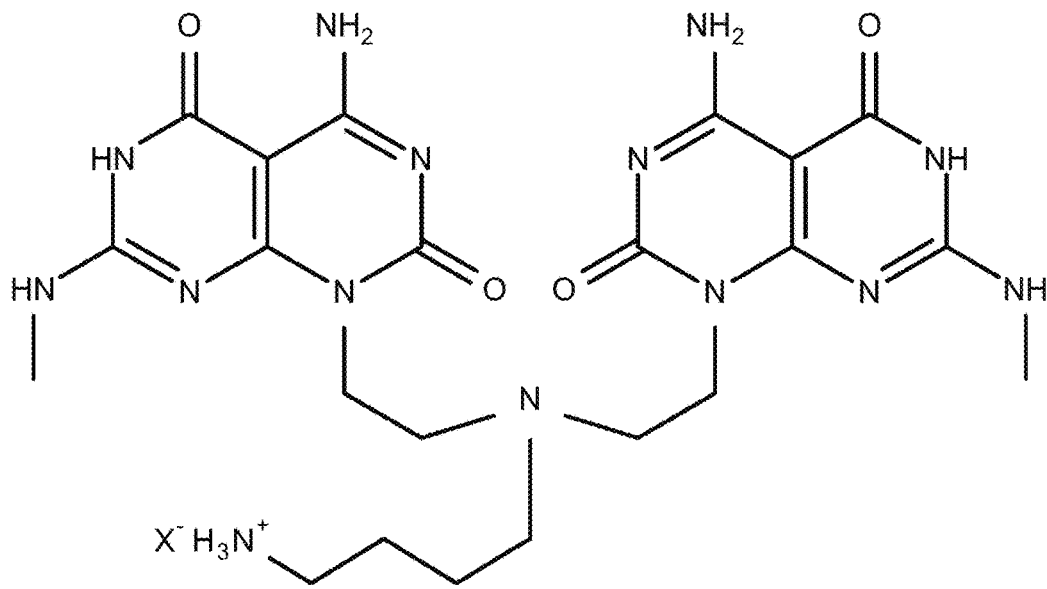
FIG. 1A shows a twin base G^C motif functionalized with an aminobutyl linker.
Figure 1B:
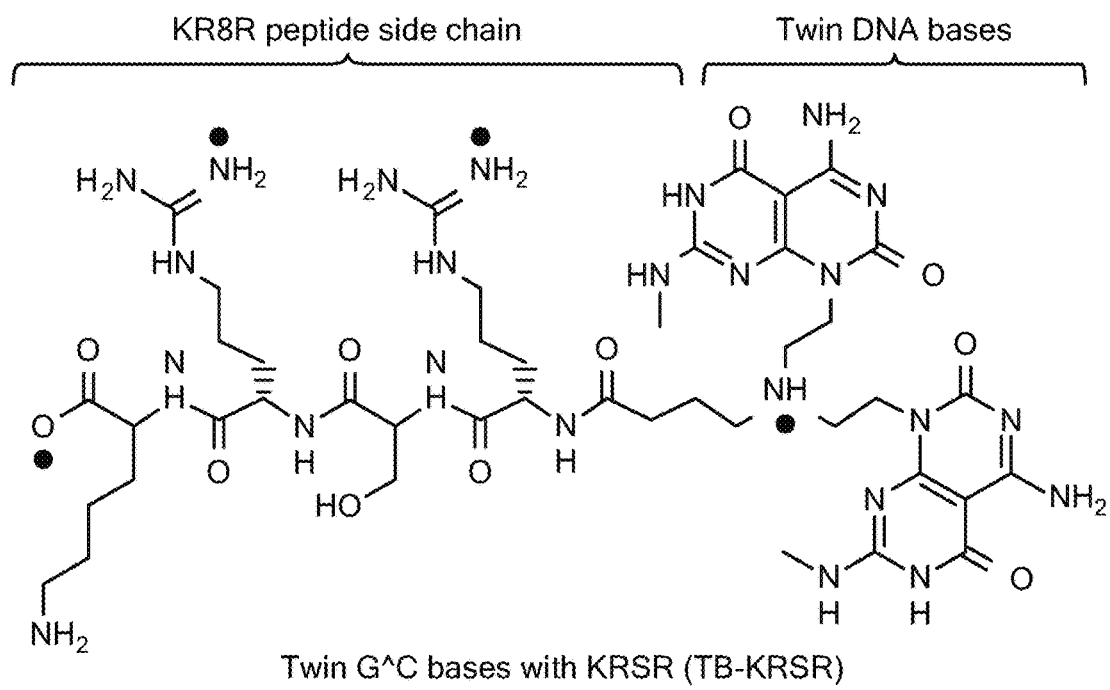
FIG. 1B shows a twin base G^C module functionalized with a propionyl linker, which is connected via a peptide bond to a KRSR (SEQ ID NO:1) tetrapeptide.
Figure 1C:
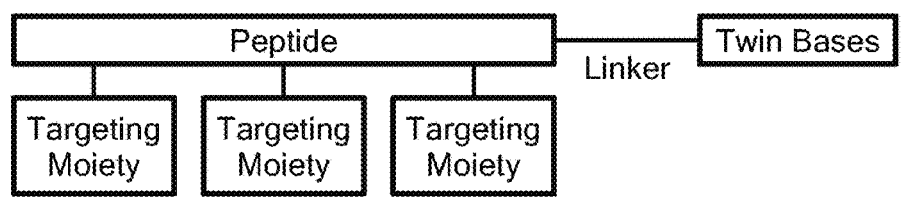
FIG. 1C shows a schematic diagram of a targeted twin base linker motif, in which the peptide moiety is covalently linked through amino acid side chains to targeting moieties.
Figure 2A:
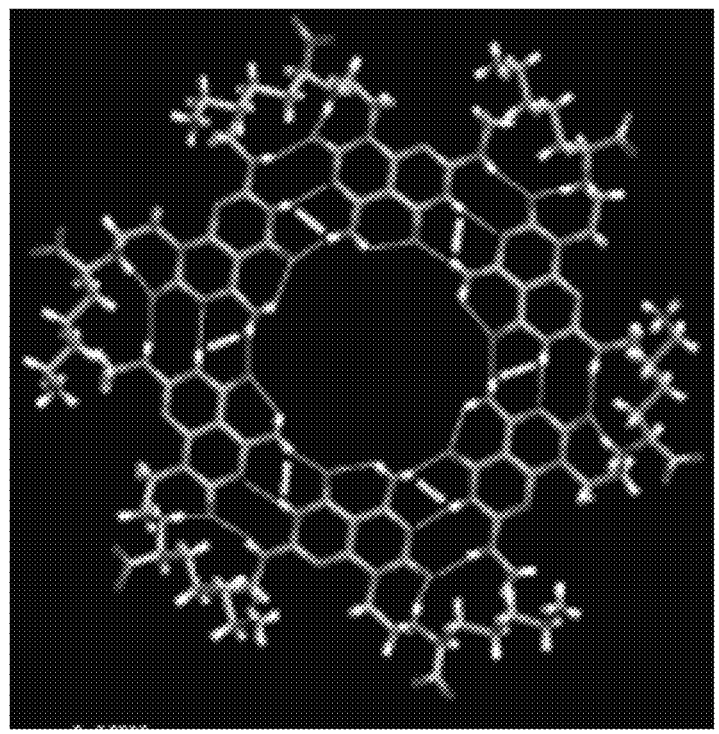
FIG. 2A shows a prior art model of a rosette structure formed by association of six twin base modules through hydrogen bonds.
Figure 2B:
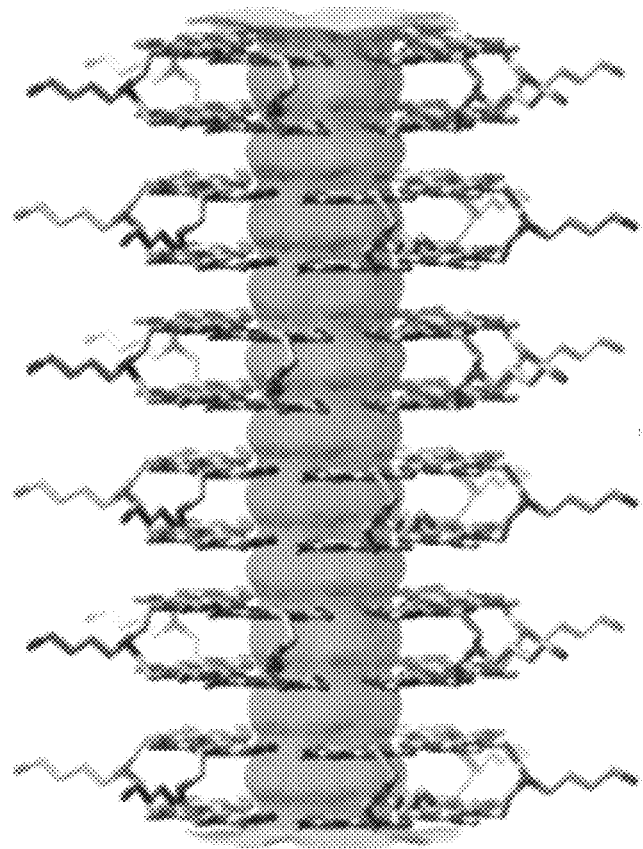
FIG. 2B shows a prior art model of a nanotubule formed by the stacking of six rosettes such as depicted in FIG. 2A.

According to the present technology, functionalized TBLs bind a target on the virus, such as the S protein of SARS-CoV-2. While not intending to limit the technology to any particular mechanism, it is believed that the TBLs form a supramolecular structure that wraps around the virus particle, in whole or in part, thereby preventing it from attaching to the target cell of the virus. A functionalized TBL monomer or motif of the present technology can have the general structure depicted in FIG. 1A, for example. The TBL monomer or motif can have a structure as depicted in Formula 1 below.

Formula 1

The twin guanine-like and cytosine-like bases can be attached via a linker, L, such as a diaminobutane moiety, a butyric acid moiety, or other linker, to a peptide. The linker can be a straight or branched chain containing from 2 to 20 carbon atoms; preferably the linker is covalently bound at a first end to a nitrogen atom of the TBL monomer and at a second end is covalently bound via a peptide linkage to the peptide moiety of the TBL. The peptide can be of any desired length, and can itself be used as a targeting moiety capable of binding to the virus binding site, or optionally can serve as a backbone to which is attached one or more optional separate targeting moieties, which can be either identical or non-identical. The targeting moieties can be, for example, peptides, oligopeptides, antibodies, including target-binding fragments thereof, or single chain recombinant antibodies, or aptamers, and can be attached via covalent bonds to amino acid side chains or a terminal $NH_2$ or COOH group of the peptide moiety, which then serves as a backbone. Alternatively, the backbone can be a nucleic acid (DNA, RNA, or synthetic), a polysaccharide such as dextran, or another polymer. Small peptides are preferred as the targeting moieties, such as peptides containing from 2 to 20 amino acids, or 2-10, 3-12, 4-10, or 4-20 amino acids, such as peptides containing 2, 3, 4, 5, 6, 7, 8, 9, or 10 amino acids.

The targeting moieties are selected to provide high affinity binding to the virus. Given that the virus particle contains multiple copies of the virus binding site, the affinity of the functionalized TBL monomers or self-assembled TBL nanostructures containing such monomers can be significantly enhanced by utilizing multiple copies of the targeting moiety, through cooperativity of binding. In addition to high affinity binding provided by one or more targeting moieties attached to the TBL monomers, the twin bases of the TBLs themselves can contribute to high affinity binding through hydrogen bonding between the bases and suitable functional groups on the virus, such as amino acids of the S protein.

For SARS-CoV-2, a preferred binding for TBLs is the receptor binding domain of the S protein, which binds to the natural target of the virus, angiotensin converting enzyme 2 (ACE2). Thus, targeting moieties can be, for example, antibodies or aptamers binding to epitopes within the receptor binding domain of S protein, or peptide fragments of ACE2 that bind to the receptor binding domain of S protein, or glycosylation sites of the S protein. The known amino acid sequence and structure of the S protein, which is described in Kumar et al., 2020, or variants thereof, can be used to select suitable epitopes for targeting. For example, fragments of the receptor binding domain (amino acids 270-510) can be used as epitopes for binding with an antibody or nucleic acid aptamer. Examples of peptides that can be used to bind to and target the novel glycosylation sites (NGTK (SEQ ID NO:3), NFTI (SEQ ID NO:4), NLTT (SEQ ID NO:5), and NTSN (SEQ ID NO:6)) of the S protein of the SARS-CoV-2 virus include: SADE (SEQ ID NO:2), SASD (SEQ ID NO:7), SASE (SEQ ID NO:8), SACD (SEQ ID NO:9), SACE (SEQ ID NO:10), SAPD (SEQ ID NO:11), SAPE (SEQ ID NO:12), SAND (SEQ ID NO:13), SANE (SEQ ID NO:14), SAQD (SEQ ID NO:15), SAQE (SEQ ID NO:16), SVSD (SEQ ID NO:17), SVSE (SEQ ID NO:18), SVCD (SEQ ID NO:19), SVCE (SEQ ID NO:20), SVPD (SEQ ID NO:21), SVPE (SEQ ID NO:22), SVND (SEQ ID NO:23), SVNE (SEQ ID NO:24), SVQD (SEQ ID NO:25), SVQE (SEQ ID NO:26), SLSD (SEQ ID NO:27), SLSE (SEQ ID NO:28), SLCD (SEQ ID NO:29), SLCE (SEQ ID NO:30), SLPD (SEQ ID NO:31), SLPE (SEQ ID NO:32), SLND (SEQ ID NO:33), SLNE (SEQ ID NO:34), SLQD (SEQ ID NO:35), SLDE (SEQ ID NO:36), SMSE (SEQ ID NO:37), SMSD (SEQ ID NO:38), SMCE (SEQ ID NO:39), SMCD (SEQ ID NO:40), SMPD (SEQ ID NO:41), SMPE (SEQ ID NO:42), SMND (SEQ ID NO:43), SMNE (SEQ ID NO:44), SMQD (SEQ ID NO:45), SMQE (SEQ ID NO:46), PASD (SEQ ID NO:47), PASE (SEQ ID NO:48), PACD (SEQ ID NO:49), PACE (SEQ ID NO:50), PAPD (SEQ ID NO:51), PAPE (SEQ ID NO:52), PAND (SEQ ID NO:53), PANE (SEQ ID NO:54), PAQD (SEQ ID NO:55), PAQE (SEQ ID NO:56), PVSD (SEQ ID NO:57), PVSE (SEQ ID NO:58), PVCD (SEQ ID NO:59), PVCE (SEQ ID NO:60), PVPD (SEQ ID NO:61), PVPE (SEQ ID NO:62), PVND (SEQ ID NO:63), PVNE (SEQ ID NO:64), PVQD (SEQ ID NO:65), PVQE (SEQ ID NO:66), PLSD (SEQ ID NO:67), PLSE (SEQ ID NO:68), PLCD (SEQ ID NO:69), PLCE (SEQ ID NO:70), PLPD (SEQ ID NO:71), PLPE (SEQ ID NO:72), PLND (SEQ ID NO:73), PLNE (SEQ ID NO:74), PLQD (SEQ ID NO:75), PLQE (SEQ ID NO:76), PMSD (SEQ ID NO:77), PMSE (SEQ ID NO:78), PMCD (SEQ ID NO:79), PMCE (SEQ ID NO:80), CASD (SEQ ID NO:81), CASE (SEQ ID NO:82), CACD (SEQ ID NO:83), CACE (SEQ ID NO:84), CAPD (SEQ ID NO:85), CAPE (SEQ ID NO:86), CAND (SEQ ID NO:87), CANE (SEQ ID NO:88), CAQD (SEQ ID NO:89), CAQE (SEQ ID NO:90), CVSD (SEQ ID NO:91), CVSE (SEQ ID NO:92), CVCD (SEQ ID NO:93), CVCE (SEQ ID NO:94), CVPD (SEQ ID NO:95), CVPE (SEQ ID NO:96), CVND (SEQ ID NO:97), CVNE (SEQ ID NO:98), CVQD (SEQ ID NO:99), CVQE (SEQ ID NO:100), CLSD (SEQ ID NO:101), CLSE (SEQ ID NO:102), CLCD (SEQ ID NO:103), CLCE (SEQ ID NO:104), CLPD (SEQ ID NO:105), CLPE (SEQ ID NO:106), CLND (SEQ ID NO:107), CLNE (SEQ ID NO:108), CLQD (SEQ ID NO:109), CLQE (SEQ ID NO:110), CMSD (SEQ ID NO:111), CMSE (SEQ ID NO:112), CMCD (SEQ ID NO:113), CMSE (SEQ ID NO:114), CMPD (SEQ ID NO:115), CMPE (SEQ ID NO:116), CMND (SEQ ID NO:117), CMNE (SEQ ID NO:118), CMQD (SEQ ID NO:119), CMQE (SEQ ID NO:120), TASD (SEQ ID NO:121), TASE (SEQ ID NO:122), TACD (SEQ ID NO:123), TACE (SEQ ID NO:124), TAPD (SEQ ID NO:125), TAPE (SEQ ID NO:126), TAND (SEQ ID NO:127), TANE (SEQ ID NO:128), TAQD (SEQ ID NO:129), TAQE (SEQ ID NO:130), TVSD (SEQ ID NO:131), TVSE (SEQ ID NO:132), TVCD (SEQ ID NO:133), TVCE (SEQ ID NO:134), TVPD (SEQ ID NO:135), TVPE (SEQ ID NO:136), TVND (SEQ ID NO:137), TVNE (SEQ ID NO:138), TVQD (SEQ ID NO:139), TVQE (SEQ ID NO:140), TLSD (SEQ ID NO:141), TLSE (SEQ ID NO:142), TLCD (SEQ ID NO:143), TLCE (SEQ ID NO:144), TLPD (SEQ ID NO:145), TLPE (SEQ ID NO:146), TLND (SEQ ID NO:147), TLNE (SEQ ID NO:148), TLQD (SEQ ID NO:149), TLQE (SEQ ID NO:150), TMSD (SEQ ID NO:151), TMSE (SEQ ID NO:152), TMCD (SEQ ID NO:153), TMCE (SEQ ID NO:154), TMPD (SEQ ID NO:155), TMPE (SEQ ID NO:156), TMND (SEQ ID NO:157), TMNE (SEQ ID NO:158), TMQD (SEQ ID NO:159), TMQE (SEQ ID NO:160), QASD (SEQ ID NO:161), QASE (SEQ ID NO:162), QVCD (SEQ ID NO:163), QVCE (SEQ ID NO:164), QVPD (SEQ ID NO:165), QVPE (SEQ ID NO:166), QVND (SEQ ID NO:167), QVNE (SEQ ID NO:168), QVQD (SEQ ID NO:169), QVQE (SEQ ID NO:170), QLSD (SEQ ID NO:171), QLSE (SEQ ID NO:172), QLCD (SEQ ID NO:173), QLCE (SEQ ID NO:174), QLPD (SEQ ID NO:175), QLPE (SEQ ID NO:176), QLND (SEQ ID NO:177), QLNE (SEQ ID NO:178), QLQD (SEQ ID NO:179), QLQE (SEQ ID NO:180), QMSD (SEQ ID NO:181), QMSE (SEQ ID NO:182), QMCD (SEQ ID NO:183), QMCE (SEQ ID NO:184), QMPD (SEQ ID NO:185), QMPE (SEQ ID NO:186), QMND (SEQ ID NO:187), QMNE (SEQ ID NO:188), QMQD (SEQ ID NO:189), QMQE (SEQ ID NO:190). These tetrapeptides, or larger peptides containing them, can be used as targeting moieties.

Similar strategies can be used to select targeting moieties for other viruses. For example, binding of TBLs to the S protein of the MERS virus can be mediated using the targeting moiety peptides MIHS (SEQ ID NO:191), AIHS (SEQ ID NO:192), VIHS (SEQ ID NO:193), IIHS (SEQ ID NO:194), LIHS (SEQ ID NO:195), FIHS (SEQ ID NO:196), YIHS (SEQ ID NO:197), WIHS (SEQ ID NO:198), MAHS (SEQ ID NO:199), MVHS (SEQ ID NO:200), MLHS (SEQ ID NO:201), MMHS (SEQ ID NO:202), MFHS (SEQ ID NO:203), MYHS (SEQ ID NO:204), MWHS (SEQ ID NO:205), AIRS (SEQ ID NO:206), AIRK (SEQ ID NO:207), AIDK (SEQ ID NO:208), AIEK (SEQ ID NO:209), MIHT (SEQ ID NO:210), MIHN (SEQ ID NO:211), and/or MIHQ (SEQ ID NO:212). Binding if TBLs to the neuraminidase of the influenza Type A virus can be obtained using as targeting moiety the peptides ASCS (SEQ ID NO:213), ATCS (SEQ ID NO:214), ANCS (SEQ ID NO:215), AQCS (SEQ ID NO:216), AVCS (SEQ ID NO:217), VSCS (SEQ ID NO:218), VTCS (SEQ ID NO:219), VNCS (SEQ ID NO:220), VQCS (SEQ ID NO:221), WCS (SEQ ID NO:222), ISCS (SEQ ID NO:223), ITCS (SEQ ID NO:224), INCS (SEQ ID NO:225), IQCS (SEQ ID NO:226), IVCS (SEQ ID NO:227), LSCS (SEQ ID NO:228), LTCS (SEQ ID NO:229), LNCS (SEQ ID NO:230), LQCS (SEQ ID NO:231), MSCS (SEQ ID NO:232), MTCS (SEQ ID NO:233), MNCS (SEQ ID NO:234), MQCS (SEQ ID NO:235), MVCS (SEQ ID NO:236), FSCS (SEQ ID NO:237), FTCS (SEQ ID NO:238), FNCS (SEQ ID NO:239), FQCS (SEQ ID NO:240), FVCS (SEQ ID NO:241), YSCS (SEQ ID NO:242), YTCS (SEQ ID NO:243), YNCS (SEQ ID NO:244), YQCS (SEQ ID NO:245), YVCS (SEQ ID NO:246), WSCS (SEQ ID NO:247), WTCS (SEQ ID NO:248), WNCS (SEQ ID NO:249), WQCS (SEQ ID NO:250), and/or WVCS (SEQ ID NO:251). Binding of TBLs to VP1-VP4 in rhinovirus can be obtained using as targeting moiety the peptides MGAQ (SEQ ID NO:252): AGAQ (SEQ ID NO:253), VGAQ (SEQ ID NO:254), IGAQ (SEQ ID NO:255), LGAQ (SEQ ID NO:256), FGAQ (SEQ ID NO:257), YGAQ (SEQ ID NO:258), WGAQ (SEQ ID NO:259), ACAQ (SEQ ID NO:260), VCAQ (SEQ ID NO:261), ICAQ (SEQ ID NO:262), LCAQ (SEQ ID NO:263), MCAQ (SEQ ID NO:264), FCAQ (SEQ ID NO:265), YCAQ (SEQ ID NO:266), WCAQ (SEQ ID NO:267), APAQ (SEQ ID NO:268), VPAQ (SEQ ID NO:269), IPAQ (SEQ ID NO:270), LPAQ (SEQ ID NO:271), FPAQ (SEQ ID NO:272), YPAQ (SEQ ID NO:273), WPAQ (SEQ ID NO:274), AGVQ (SEQ ID NO:275), VGVQ (SEQ ID NO:276), IGVQ (SEQ ID NO:277), LGVQ (SEQ ID NO:278), FGVQ (SEQ ID NO:279), YGVQ (SEQ ID NO:280), WGVQ (SEQ ID NO:281), ACVQ (SEQ ID NO:282), VCVQ (SEQ ID NO:283), ICVQ (SEQ ID NO:284), LCVQ (SEQ ID NO:285), MCVQ (SEQ ID NO:286), FCVQ (SEQ ID NO:287), YCVQ (SEQ ID NO:288), WCVQ (SEQ ID NO:289), APVQ (SEQ ID NO:290), VPVQ (SEQ ID NO:291), IPVQ (SEQ ID NO:292), LPVQ (SEQ ID NO:293), FPVQ (SEQ ID NO:294), YPVQ (SEQ ID NO:295), and/or WPVQ (SEQ ID NO:296).

The TBL monomers and nanostructures of the present technology can also serve to misdirect the targeted virus. For example, either the peptide moiety of the functionalized TBL monomer or one or more of the targeting moieties attached thereto can bind to a selected cellular receptor so as to enhance binding of the virus to receptors that it cannot use to enter cells, or to direct it to cells of the immune system that can destroy it.

The present technology also includes a method to aid in treating or preventing a viral infection. The method includes administering to a subject in need thereof a composition containing a functionalized TBL monomer as described above, and/or a nanostructure formed from one or more types of such functionalized TBL monomers. The subject can be a human or other mammal having or suspected of having or acquiring a viral infection, including COVID-19, SARS, influenza, ebola, rhinovirus, hepatitis B or hepatitis C, MERS, HIV, adenovirus, measles, mumps, chickenpox, or another viral infection. Preferably, the functionalized TBL monomers are administered as an injectable liquid formulation or as an aerosol formulation for direct intrapulmonary administration, wherein the monomers self-assemble within the subject's body to form biodegradable nanostructures with antiviral activity. Alternatively, the monomers can be pre-assembled to form nanostructures prior to administration.

EXAMPLES

Example 1. Inhibition of Infection of Mammalian Cells by Pseudovirus Expressing SARS-CoV-2 Spike Protein Screening studies confirmed binding of TBLs functionalized with the peptide SADE (SEQ ID NO:2) as targeting moiety to the heat-inactivated SARS-CoV-2 spike (S) protein. Binding affinity for SARS-CoV-2 envelope (E) protein by the SADE (SEQ ID NO:2) peptide was also indicated, suggesting that it would serve as a strong targeting moiety, even in the presence of mutations of the S protein. Scrambling of the amino acid sequence of SADE (SEQ ID NO:2) eliminated the binding affinity. Other peptide sequences that were identified as binding SARS-CoV-2 S protein were SASD (SEQ ID NO:7), SASE (SEQ ID NO:8), and SACD (SEQ ID NO:9).

The objective of the present in vitro experiments was to determine the ability of the same TBLs to passivate infection of mammalian cells from a pseudo SARS-CoV-2 virus. The pseudovirus was supplied by Creative Diagnostics. Results of this in vitro study showed that TBLs functionalized with SADE (SEQ ID NO:2) (i.e., the TBS monomer of Formula 1 wherein L=SADE (SEQ ID NO:2) peptide, no further targeting moieties) can passivate the SARS-CoV-2 pseudovirus and inhibit its ability to infect mammalian cells.

Figure 3:
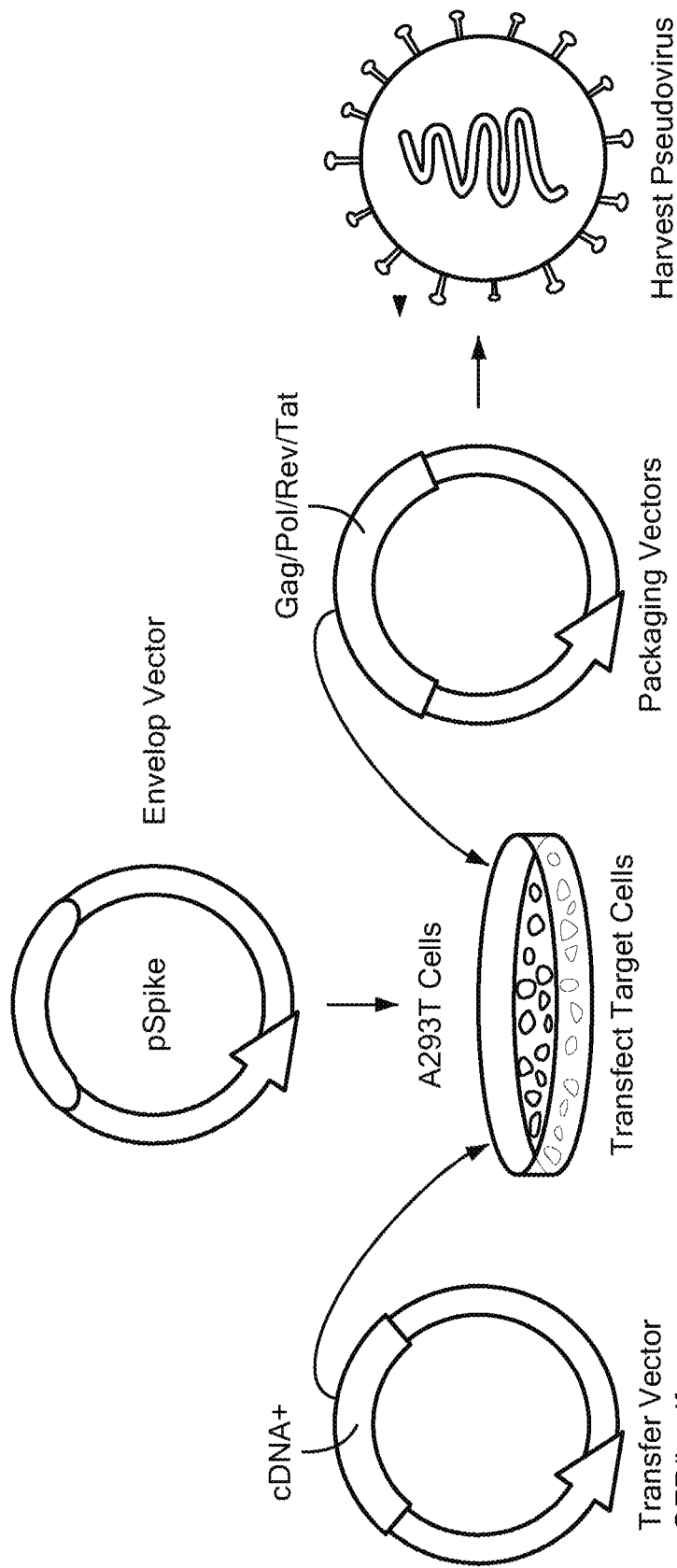
FIG. 3 shows a schematic representation of a process of preparing a pseudovirus containing a desired virus spike protein and expressing green fluorescent protein (GFP) or luciferase after infection of target cells.

A lentiviral SARS-CoV-2 pseudovirus was used for the study. While live SARS-CoV-2 has to be handled under biosafety level 3 conditions, which has hindered the development of vaccines and therapeutics, pseudoviruses are useful virological tools because of their safety and versatility, because the pseudovirus is restricted to a single round of replication and can be handled using BSL-2 containment practices. The pseudovirus expressed GFP in infected cells, allowing infection to be measured with a fluorimeter. The pseudotyped Luciferase/GFP rSARS-CoV-2 displayed antigenically correct spike protein (Wuhan-Hu-1 strain or D614G mutant) pseudotyped on replication-incompetent virus particles that contain a heterologous lentiviral (HIV) core and were capable of a single round of infection. Pseudotyped Luciferase/GFP rSARS-CoV-2 Spike were produced in HEK-293T cells using three separate plasmids (see FIG. 3), and encoded the spike protein, a lentiviral gag polyprotein, and the GFP reporter gene.

HEK293T cells were used for transfection by the pseudovirus. This cell line is constructed by transduction of human angiotensin I converting enzyme 2 (ACE2) into HEK293T cells, followed by stable cell selection. This cell line can be used for in vitro screening and characterization of drug candidates against SARS-CoV-2 because it expresses ACE2 which serves as the host receptor for SARS-CoV-2.

TBLs functionalized with SADE (SEQ ID NO:2) were added at various concentrations (from 0 to 0.001 mg/ml) to selected concentrations of a SARS-CoV-2 pseudovirus (10 to $10^6$ copies/µL) added to HEK293T cells seeded at $10^4$ cells per well. Standard cell culture medium (DMEM+10% FBS) was added to the wells. The TBLs were then allowed to interact with the pseudovirus and cells for periods of time from 15 minutes to 4 hours under standard incubator conditions. After the prescribed time period, the samples were analyzed using a fluorimeter. All experiments were conducted in triplicate and repeated at three different time periods with appropriate controls, including no TBLs, no cells, and no pseudovirus. Differences between fluorescence intensity were assessed using ANOVA and student's t test with $p<0.01$ considered statistically significant.

Figure 4A:
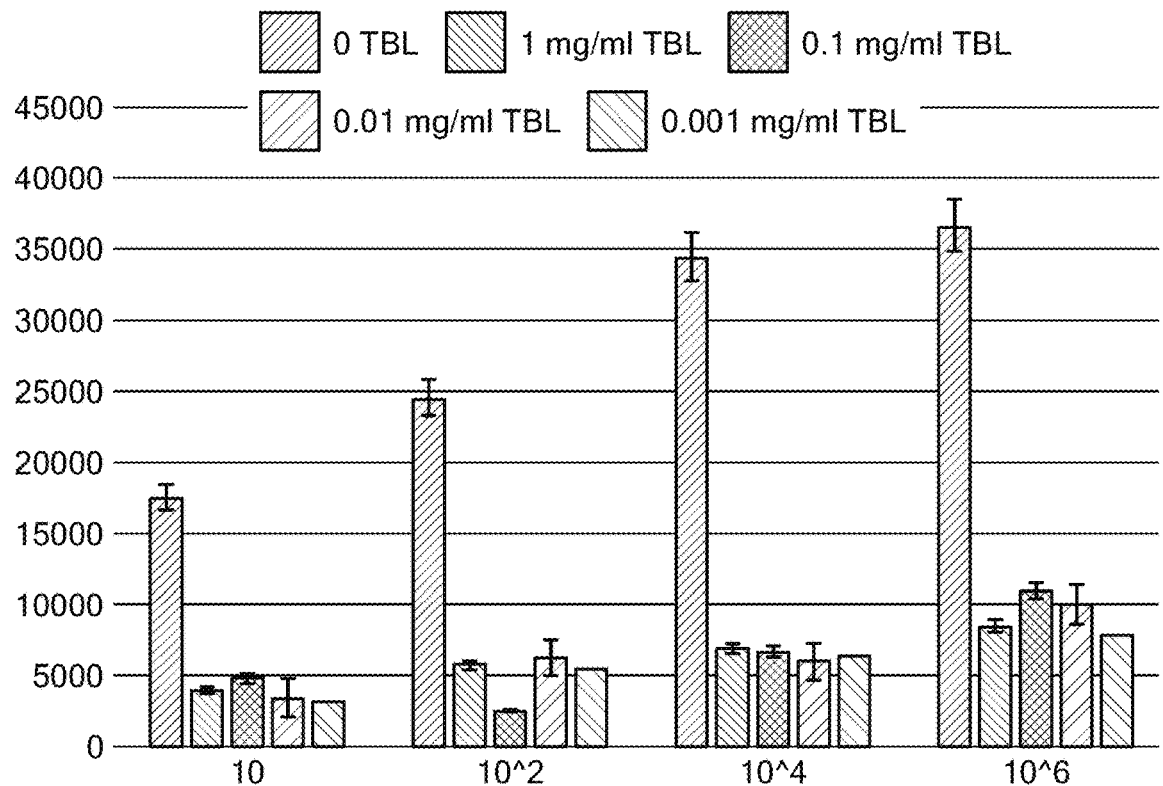
FIGS. 4A-4C show results of infecting HEK293T cells with a pseudovirus displaying the spike protein of SARS-CoV-2, and expressing GFP in the infected cells. The vertical axis represents arbitrary units of fluorescence, and the horizontal groupings represent pseudovirus concentration (copies/μL) added to the medium. Each grouping of bars shows the concentration of TBL present (left to right: 0, 1 mg/mL, 0.1 mg/mL, 0.01 mg/mL, and 0.001 mg/mL). All amounts of TBL were significantly different (p<0.01) from no TBL. Number of cells was constant for all assays. TBL was functionalized with SADE (SEQ ID NO:2) (SEQ ID NO:2) peptide. Time of incubation of the cells with pseudovirus was 15 min (FIG. 4A), 1 hour (FIG. 4B), or 4 hours (FIG. 4C). All controls (no cells, no pseudovirus) showed no fluorescence.
Figure 4B:
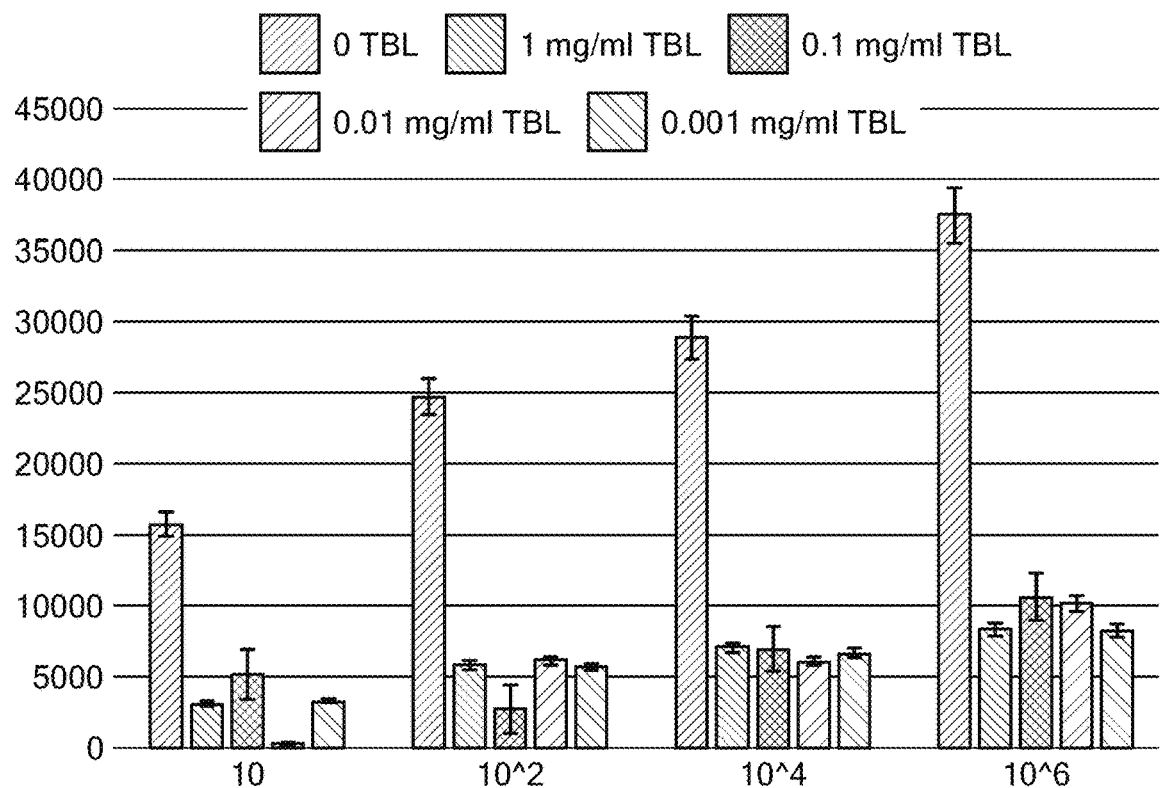
Figure 4C:
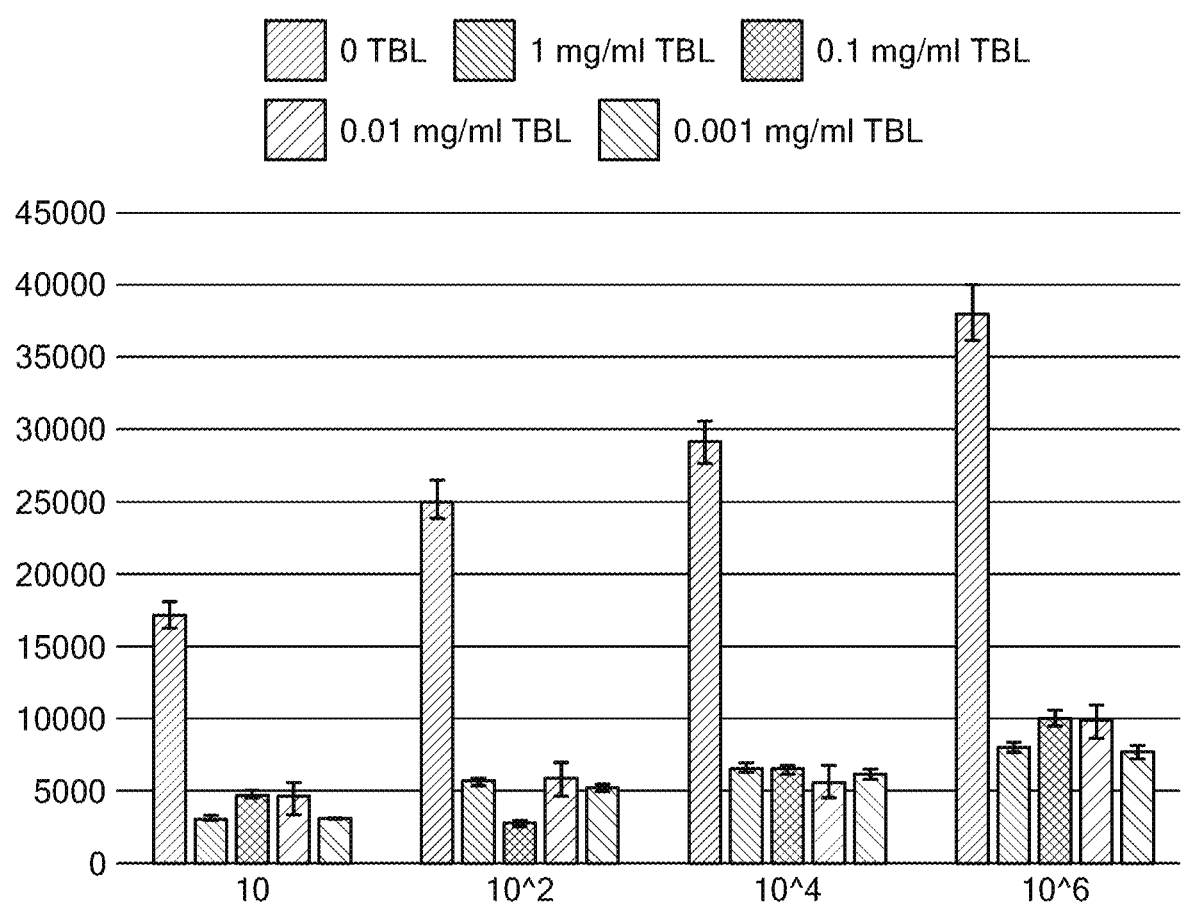

Results of this study showed that the TBLs functionalized with SADE (SEQ ID NO:2) significantly inhibited SARS-CoV-2 pseudovirus infection of the mammalian cells at all concentrations and time periods tested (see FIGS. 4A-4C). Inhibition ranged from 64% to 98%. Importantly, a pseudovirus concentration effect was observed; when more pseudovirus was added to the cultures, more infection was found. However, no strong TBL concentration effect was not observed. All controls confirmed the validity of the experimental system.

Figure 5A:
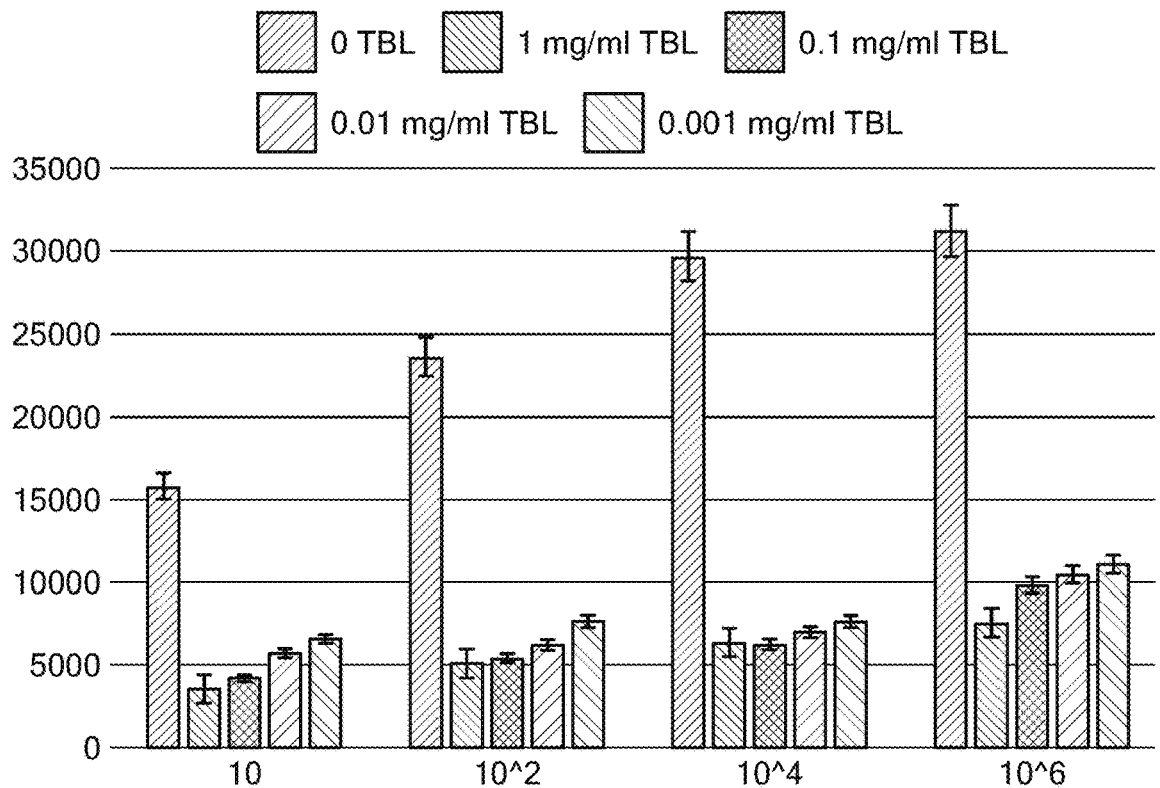
FIGS. 5A-5C show results of infecting HEK293T cells with a pseudovirus displaying the spike protein of the B117 variant of SARS-CoV-2, and expressing GFP in the infected cells. The vertical axis represents arbitrary units of fluorescence, and the horizontal groupings represent pseudovirus concentration (copies/μL) added to the medium. Each grouping of bars shows the concentration of TBL present (left to right: 0, 1 mg/mL, 0.1 mg/mL, 0.01 mg/mL, and 0.001 mg/mL). All amounts of TBL were significantly different (p<0.01) from no TBL. Number of cells was constant for all assays. TBL was functionalized with SADE (SEQ ID NO:2) peptide. Time of incubation of the cells with pseudovirus was 15 min (FIG. 5A), 1 hour (FIG. 5B), or 4 hours (FIG. 5C).
Figure 5B:
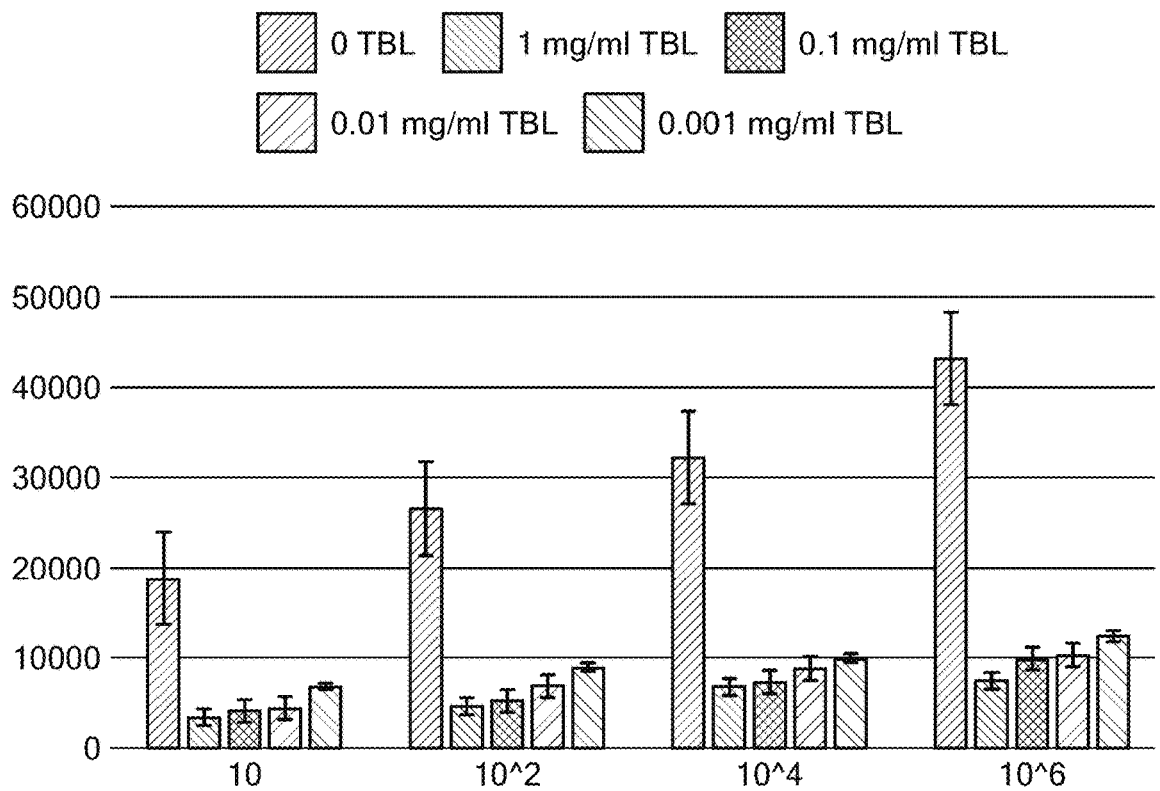
Figure 5C:
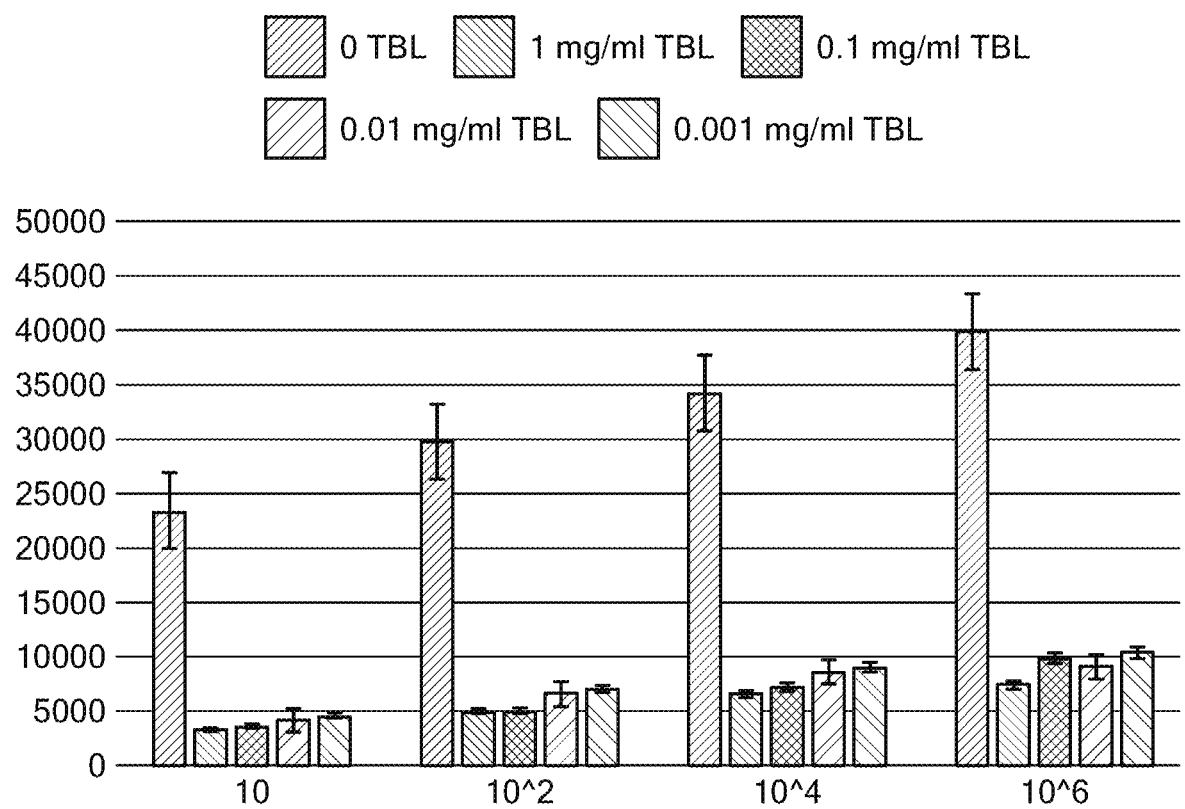
Figure 6A:
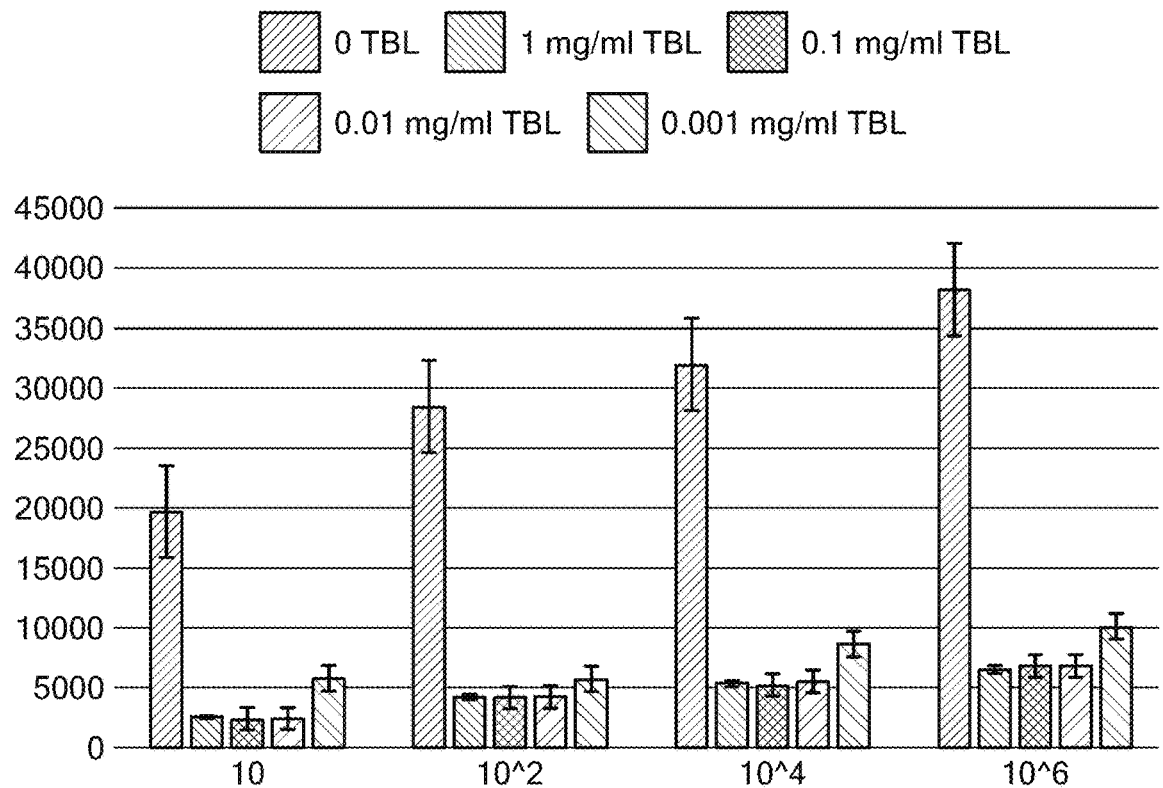
FIGS. 6A-6C show results of infecting HEK293T cells with a pseudovirus displaying the spike protein of the 501 YV2 variant of SARS-CoV-2, and expressing GFP in the infected cells. The vertical axis represents arbitrary units of fluorescence, and the horizontal groupings represent pseudovirus concentration (copies/μL) added to the medium. Each grouping of bars shows the concentration of TBL present (left to right: 0, 1 mg/mL, 0.1 mg/mL, 0.01 mg/mL, and 0.001 mg/mL). All amounts of TBL were significantly different (p<0.01) from no TBL. Number of cells was constant for all assays. TBL was functionalized with SADE (SEQ ID NO:2) peptide. Time of incubation of the cells with pseudovirus was 15 min (FIG. 6A), 1 hour (FIG. 6B), or 4 hours (FIG. 6C).
Figure 6B:
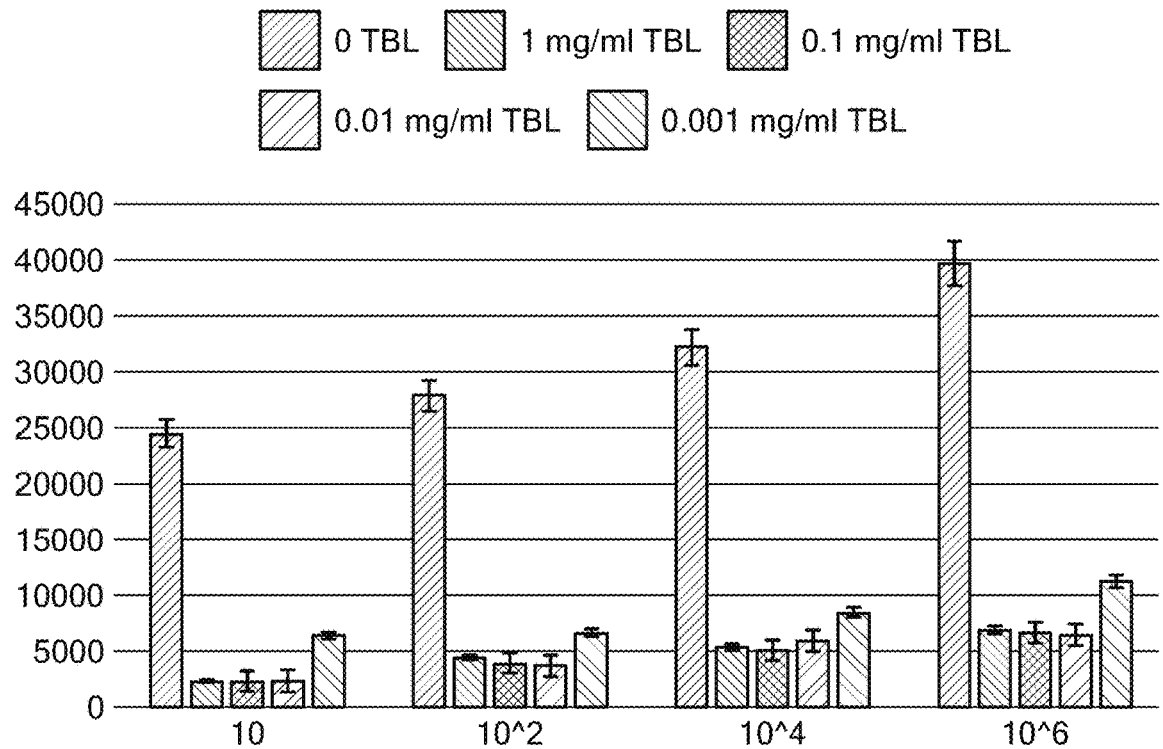
Figure 6C:
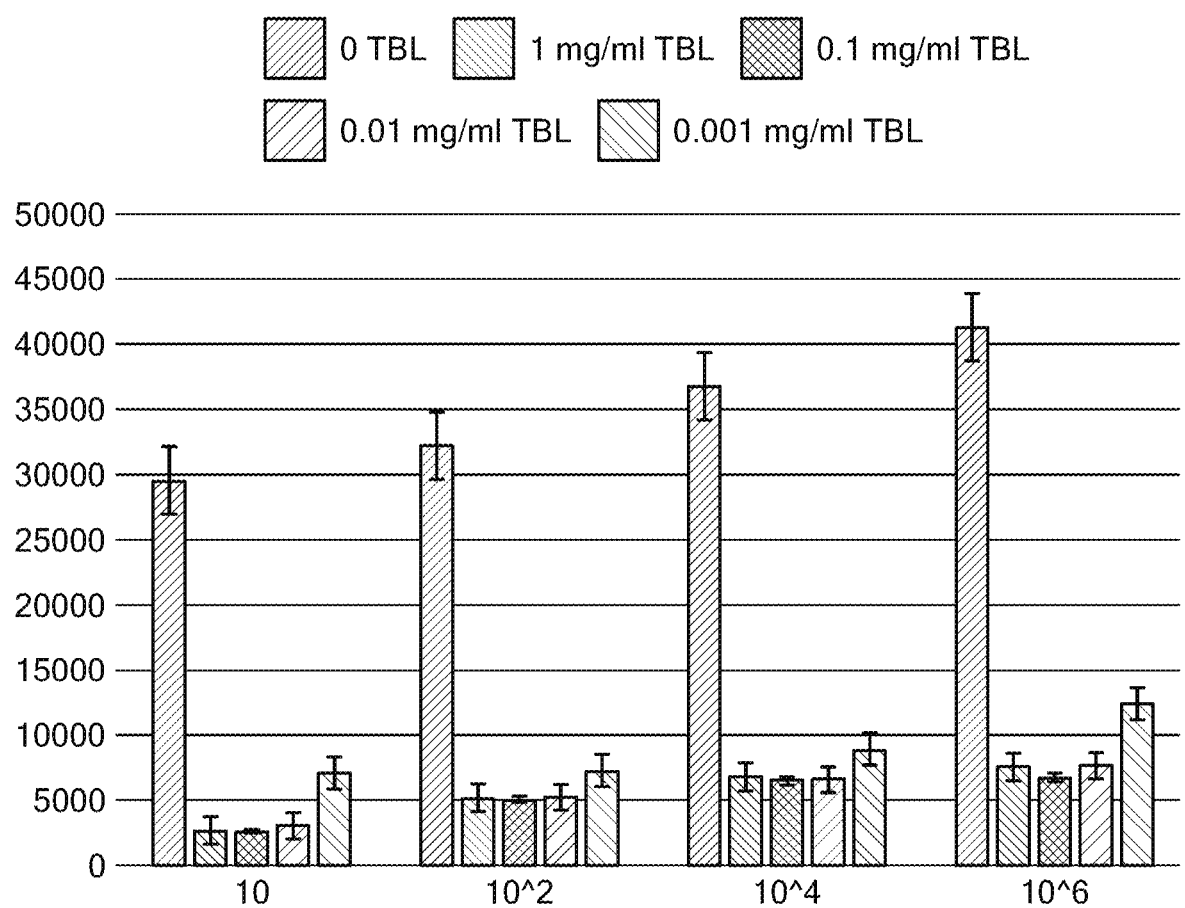

Example 2. Inhibition of Infection of Mammalian Cells by Pseudovirus Expressing Variants of SARS-CoV-2 Spike Protein The experiment described in Example 1 was repeated using a pseudovirus possessing the S protein of the B.1.1.7 variant (see FIGS. 5A-5C) or the 501Y.V2 variant (FIGS. 6A-6C). TBLs were functionalized with SADE (SEQ ID NO:2) (i.e., the TBS monomer of Formula 1 wherein L=SADE (SEQ ID NO:2) peptide, no further targeting moieties).

Inhibition of infection by the B.1.1.7 (UK) variant was dose dependent with respect to the amount of functionalized TBL added, and longer incubation produced somewhat greater inhibition, with the TBL effect being essentially maximum at 1 hour incubation. Inhibition ranged from 76% to 86%.

Inhibition of infection by the 501Y.V2 (South African) variant also showed dose dependency with respect to the amount of functionalized TBL. One hour incubation again produced a maximal effect, and inhibition ranged from producing from 82% to 91% inhibition of infection.

Figure 7:
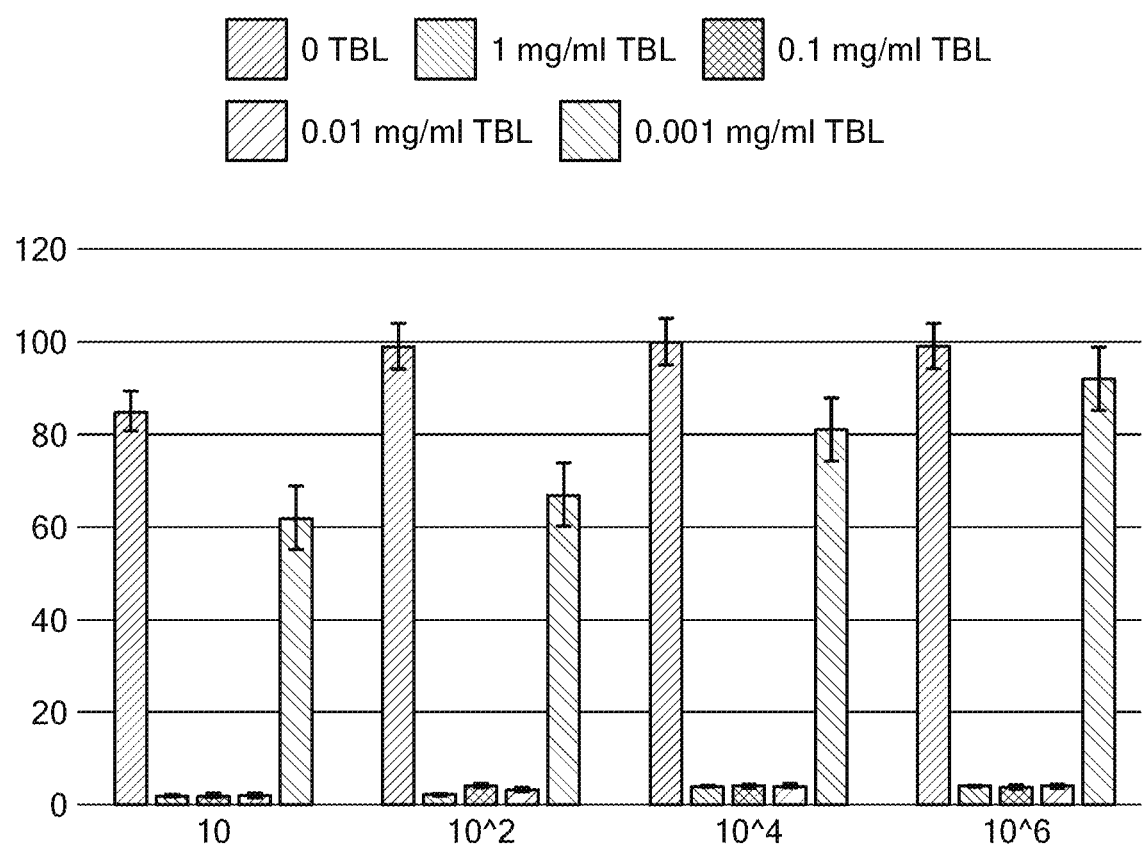
FIG. 7 shows results of an experiment to test the ability of functionalized TBL-SADE (SEQ ID NO:2) to protect normal human adult dermal fibroblasts (HDFa from ATCC) from death caused by infection with rhinovirus. Vertical axis shows fluorescence (arbitrary units; Live and Dead Cell Assay by Abcam) indicating dead cells, while the horizontal axis shows the rhinovirus concentration in copies/μL. Concentrations of 0.01 to 1 mg/mL of TBL-SADE inhibited cell death by 96% to 98%.
Figure 8A:
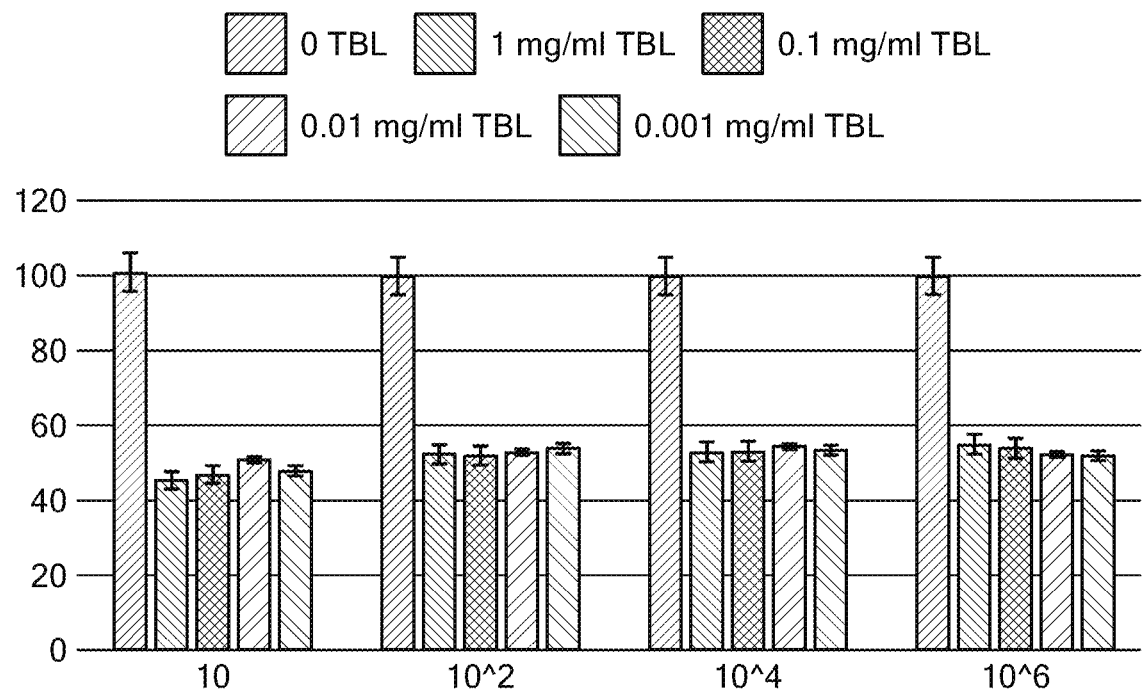
FIGS. 8A-8B show protection by TBL-SADE of human adult dermal fibroblasts from death by infection with influenza A (FIG. 8A) or influenza B (FIG. 8B) virus. Inhibition was 45% to 55% for influenza A and 42% to 48% for influenza B. Vertical axis shows fluorescence (arbitrary units; Live and Dead Cell Assay by Abcam) indicating dead cells, while the horizontal axis shows the virus concentration in copies/µL
Figure 8B:
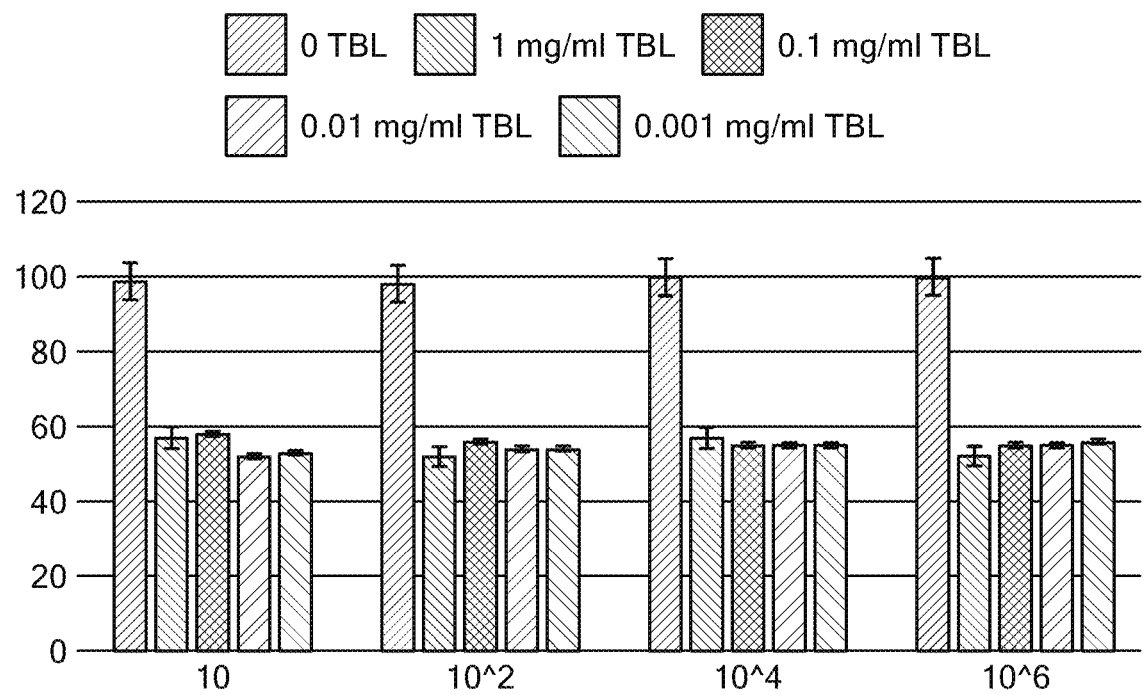

Example 3. Inhibition of Fibroblast Death from Infection by Rhinovirus or Influenza Virus An experiment similar to that described in Example 1 was performed to test whether TBL functionalized with SADE could protect human dermal fibroblasts from death be infection with rhinovirus, influenza A virus, or influenza B virus. A fluorescent dye was used to indicate dead cells in which fluorescence intensity is proportional to the number of dead cells. The results are shown in FIG. 7 for rhinovirus infection, in FIG. 8A for influenza A infection, and in FIG. 8B for influenza B infection. Death from rhinovirus infection was inhibited by 96% to 98%, while death from influenza virus infection was inhibited by 45% to 55% for influenza A and 42% to 48% for influenza B virus over the range of TBL concentrations tested (0.001 to 1 mg/mL).

A sequence listing is provided as an ASCII text file named "Sequence-Listing-ST25-as-filed-23Jun2021-19815-0693" created on 23 Jun. 2021 and having a size of 45084 bytes. The ASCII text file is hereby incorporated by reference in the application.

REFERENCES

R. Al-Attabi, et al., Catalytic electrospun nano-composite membranes for virus capture and remediation. Separation and Purification Technology 229, 115806 (2019).

H. Fenniri, et al., Helical Rosette Nanotubes: Design, Self-Assembly, and Characterization. J. Am. Chem. Soc. 123, 3854-3855 (2001).

S. Kumar et al., Structural, glycosylation and antigenic variation between 2019 novel coronavirus (2019-nCoV) and SARS coronavirus (SARS-CoV). Virus Dis. doi.org/10.1007/s13337-020.00571-5, 5 Mar. 2020

S. Song, et al., Self-assembled rosette nanotubes for incorporating hydrophobic drugs in physiological environments. Int. J. Nanomedicine 6, 101-107 (2011).

The invention claimed is:

1. An antiviral composition comprising a plurality of functionalized twin base linker (TBL) molecules having the general structure

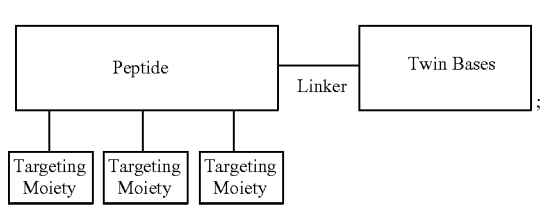

wherein the twin bases comprise a structure according to Formula 1

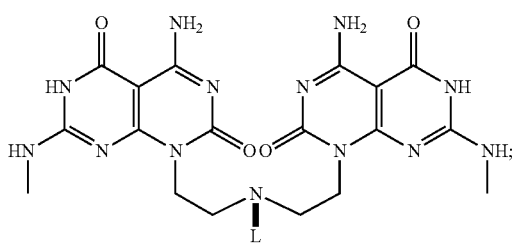

Formula 1 wherein L is the linker and comprises carbon, nitrogen, and/or oxygen atoms and has a chain length from about 4 to about 20 atoms;

wherein the peptide moiety serves as a backbone and contains from about 2 to about 20 L- and/or D-amino acids; and wherein one or more targeting moieties are covalently linked to the peptide, and wherein each of the one or more targeting moieties consists of from 3 to 12 amino acids and is capable of specifically binding a surface-accessible protein of a virus, thereby deactivating the virus.

2. The antiviral composition of claim 1, wherein the peptide comprises one or more amino acids that are positively charged at pH 7 and/or one or more amino acids that are negatively charged at pH 7.

3. The antiviral composition of claim 1, wherein each targeting moiety peptide has an amino acid sequence that is distinct from that of the peptide moiety.

4. The antiviral composition of claim 1, wherein the one or more targeting moieties bind to a virus spike protein, a virus envelope protein, or both.

5. The antiviral composition of claim 4, wherein the one or more targeting moieties comprise a peptide selected from the group consisting of SADE (SEQ ID NO:2), SASD (SEQ ID NO:7), SASE (SEQ ID NO:8), and SACD (SEQ ID NO:9).

6. The antiviral composition of claim 1, comprising functionalized TBL molecules in monomeric form.

7. The antiviral composition of claim 1, comprising functionalized TBL molecules in form of a supramolecular assembly.

8. The antiviral composition of claim 1, wherein the targeting moieties bind to a protein of SARS-COV-2 virus.

9. The antiviral composition of claim 8, wherein the targeting moieties bind to S protein of SARS-COV-2 virus.

10. The antiviral composition of claim 9, wherein the targeting moieties also bind to E protein of SARS-COV-2 virus.

11. The antiviral composition of claim 1, wherein the functionalized TBL molecules, or a supramolecular assembly comprising the functionalized TBL molecules, is capable of inhibiting entry of the virus into a mammalian cell.

12. The antiviral composition of claim 1, wherein the functionalized TBL molecules, or a supramolecular assembly comprising the functionalized TBL molecules, is capable of inhibiting death of mammalian cells infected by the virus.

13. The antiviral composition of claim 1, wherein the composition is for use in treating or preventing a viral infection.

14. The antiviral composition of claim 13, wherein the viral infection is caused by a virus selected from the group consisting of a corona virus, SARS-COV-2, influenza A virus, influenza B virus, an ebola virus, HIV, an adenovirus, a rhinovirus, hepatitis B virus, hepatitis C virus, MERS virus, measles virus, mumps virus, and chickenpox virus.

15. The antiviral composition of claim 13, wherein the composition is for use in treating or preventing two or more viral infections selected from the group consisting of a corona virus, SARS-COV-2, influenza A virus, influenza B virus, an ebola virus, HIV, an adenovirus, a rhinovirus, hepatitis B virus, hepatitis C virus, MERS virus, measles virus, mumps virus, and chickenpox virus.

16. The antiviral composition of claim 15, wherein the composition is for treating or preventing infection by SARS COV-2, influenza A virus, influenza B virus, and rhinovirus.

17. A method to aid in treating or preventing a viral infection, the method comprising administering the antiviral composition of claim 1 to a subject in need thereof.

18. The method of claim 17, wherein the viral infection is caused by a virus selected from the group consisting of a corona virus, SARS-COV-2, influenza A virus, influenza B virus, an ebola virus, HIV, adenovirus, a rhinovirus, hepatitis B virus, hepatitis C virus, MERS virus, measles virus, mumps virus, and chickenpox virus.

19. The method of claim 18, wherein the virus is SARS-COV-2.

20. The method of claim 17, wherein cellular entry of a virus, virus replication, and/or one or more symptoms of the viral infection are reduced or prevented in the subject.

* * * * *

SEQUENCE LISTING

```
<160> NUMBER OF SEQ ID NOS: 296

<210> SEQ ID NO 1
<211> LENGTH: 4
<212> TYPE: PRT
<213> ORGANISM: Artificial Sequence
<220> FEATURE:
<223> OTHER INFORMATION: Targeting moiety

<400> SEQUENCE: 1

Lys Arg Ser Arg
1

<210> SEQ ID NO 2
<211> LENGTH: 4
<212> TYPE: PRT
<213> ORGANISM: Artificial Sequence
<220> FEATURE:
<223> OTHER INFORMATION: Targeting moiety

<400> SEQUENCE: 2

Ser Ala Asp Glu
1

<210> SEQ ID NO 3
<211> LENGTH: 4
<212> TYPE: PRT
<213> ORGANISM: Artificial Sequence
<220> FEATURE:
<223> OTHER INFORMATION: Targeting moiety

<400> SEQUENCE: 3

Asn Gly Thr Lys
1

<210> SEQ ID NO 4
<211> LENGTH: 4
<212> TYPE: PRT
<213> ORGANISM: Artificial Sequence
<220> FEATURE:
<223> OTHER INFORMATION: Targeting moiety

<400> SEQUENCE: 4

Asn Phe Thr Ile
1

<210> SEQ ID NO 5
<211> LENGTH: 4
<212> TYPE: PRT
<213> ORGANISM: Artificial Sequence
```

```
<220> FEATURE:
<223> OTHER INFORMATION: Targeting moiety

<400> SEQUENCE: 5

Asn Leu Thr Thr
1

<210> SEQ ID NO 6
<211> LENGTH: 4
<212> TYPE: PRT
<213> ORGANISM: Artificial Sequence
<220> FEATURE:
<223> OTHER INFORMATION: Targeting moiety

<400> SEQUENCE: 6

Asn Thr Ser Asn
1

<210> SEQ ID NO 7
<211> LENGTH: 4
<212> TYPE: PRT
<213> ORGANISM: Artificial Sequence
<220> FEATURE:
<223> OTHER INFORMATION: Targeting moiety

<400> SEQUENCE: 7

Ser Ala Ser Asp
1

<210> SEQ ID NO 8
<211> LENGTH: 4
<212> TYPE: PRT
<213> ORGANISM: Artificial Sequence
<220> FEATURE:
<223> OTHER INFORMATION: Targeting moiety

<400> SEQUENCE: 8

Ser Ala Ser Glu
1

<210> SEQ ID NO 9
<211> LENGTH: 4
<212> TYPE: PRT
<213> ORGANISM: Artificial Sequence
<220> FEATURE:
<223> OTHER INFORMATION: Targeting moiety

<400> SEQUENCE: 9

Ser Ala Cys Asp
1

<210> SEQ ID NO 10
<211> LENGTH: 4
<212> TYPE: PRT
<213> ORGANISM: Artificial Sequence
<220> FEATURE:
<223> OTHER INFORMATION: Targeting moiety

<400> SEQUENCE: 10

Ser Ala Cys Glu
1

<210> SEQ ID NO 11
<211> LENGTH: 4
<212> TYPE: PRT
<213> ORGANISM: Artificial Sequence
<220> FEATURE:
```

```
<223> OTHER INFORMATION: Targeting moiety

<400> SEQUENCE: 11

Ser Ala Pro Asp
1

<210> SEQ ID NO 12
<211> LENGTH: 4
<212> TYPE: PRT
<213> ORGANISM: Artificial Sequence
<220> FEATURE:
<223> OTHER INFORMATION: Targeting moiety

<400> SEQUENCE: 12

Ser Ala Pro Glu
1

<210> SEQ ID NO 13
<211> LENGTH: 4
<212> TYPE: PRT
<213> ORGANISM: Artificial Sequence
<220> FEATURE:
<223> OTHER INFORMATION: Targeting moiety

<400> SEQUENCE: 13

Ser Ala Asn Asp
1

<210> SEQ ID NO 14
<211> LENGTH: 4
<212> TYPE: PRT
<213> ORGANISM: Artificial Sequence
<220> FEATURE:
<223> OTHER INFORMATION: Targeting moiety

<400> SEQUENCE: 14

Ser Ala Asn Glu
1

<210> SEQ ID NO 15
<211> LENGTH: 4
<212> TYPE: PRT
<213> ORGANISM: Artificial Sequence
<220> FEATURE:
<223> OTHER INFORMATION: Targeting moiety

<400> SEQUENCE: 15

Ser Ala Gln Asp
1

<210> SEQ ID NO 16
<211> LENGTH: 4
<212> TYPE: PRT
<213> ORGANISM: Artificial Sequence
<220> FEATURE:
<223> OTHER INFORMATION: Targeting moiety

<400> SEQUENCE: 16

Ser Ala Gln Glu
1

<210> SEQ ID NO 17
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 17

Ser Val Ser Asp
1

<210> SEQ ID NO 18
<211> LENGTH: 4
<212> TYPE: PRT
<213> ORGANISM: Artificial Sequence
<220> FEATURE:
<223> OTHER INFORMATION: Targeting moiety

<400> SEQUENCE: 18

Ser Val Ser Glu
1

<210> SEQ ID NO 19
<211> LENGTH: 4
<212> TYPE: PRT
<213> ORGANISM: Artificial Sequence
<220> FEATURE:
<223> OTHER INFORMATION: Targeting moiety

<400> SEQUENCE: 19

Ser Val Cys Asp
1

<210> SEQ ID NO 20
<211> LENGTH: 4
<212> TYPE: PRT
<213> ORGANISM: Artificial Sequence
<220> FEATURE:
<223> OTHER INFORMATION: Targeting moiety

<400> SEQUENCE: 20

Ser Val Cys Glu
1

<210> SEQ ID NO 21
<211> LENGTH: 4
<212> TYPE: PRT
<213> ORGANISM: Artificial Sequence
<220> FEATURE:
<223> OTHER INFORMATION: Targeting moiety

<400> SEQUENCE: 21

Ser Val Pro Asp
1

<210> SEQ ID NO 22
<211> LENGTH: 4
<212> TYPE: PRT
<213> ORGANISM: Artificial Sequence
<220> FEATURE:
<223> OTHER INFORMATION: Targeting moiety

<400> SEQUENCE: 22

Ser Val Pro Glu
1

<210> SEQ ID NO 23
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 23

Ser Val Asn Asp
1

<210> SEQ ID NO 24
<211> LENGTH: 4
<212> TYPE: PRT
<213> ORGANISM: Artificial Sequence
<220> FEATURE:
<223> OTHER INFORMATION: Targeting moiety

<400> SEQUENCE: 24

Ser Val Asn Glu
1

<210> SEQ ID NO 25
<211> LENGTH: 4
<212> TYPE: PRT
<213> ORGANISM: Artificial Sequence
<220> FEATURE:
<223> OTHER INFORMATION: Targeting moiety

<400> SEQUENCE: 25

Ser Val Gln Asp
1

<210> SEQ ID NO 26
<211> LENGTH: 4
<212> TYPE: PRT
<213> ORGANISM: Artificial Sequence
<220> FEATURE:
<223> OTHER INFORMATION: Targeting moiety

<400> SEQUENCE: 26

Ser Val Gln Glu
1

<210> SEQ ID NO 27
<211> LENGTH: 4
<212> TYPE: PRT
<213> ORGANISM: Artificial Sequence
<220> FEATURE:
<223> OTHER INFORMATION: Targeting moiety

<400> SEQUENCE: 27

Ser Leu Ser Asp
1

<210> SEQ ID NO 28
<211> LENGTH: 4
<212> TYPE: PRT
<213> ORGANISM: Artificial Sequence
<220> FEATURE:
<223> OTHER INFORMATION: Targeting moiety

<400> SEQUENCE: 28

Ser Leu Ser Glu
1

<210> SEQ ID NO 29
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 29

Ser Leu Cys Asp
1

<210> SEQ ID NO 30
<211> LENGTH: 4
<212> TYPE: PRT
<213> ORGANISM: Artificial Sequence
<220> FEATURE:
<223> OTHER INFORMATION: Targeting moiety

<400> SEQUENCE: 30

Ser Leu Cys Glu
1

<210> SEQ ID NO 31
<211> LENGTH: 4
<212> TYPE: PRT
<213> ORGANISM: Artificial Sequence
<220> FEATURE:
<223> OTHER INFORMATION: Targeting moiety

<400> SEQUENCE: 31

Ser Leu Pro Asp
1

<210> SEQ ID NO 32
<211> LENGTH: 4
<212> TYPE: PRT
<213> ORGANISM: Artificial Sequence
<220> FEATURE:
<223> OTHER INFORMATION: Targeting moiety

<400> SEQUENCE: 32

Ser Leu Pro Glu
1

<210> SEQ ID NO 33
<211> LENGTH: 4
<212> TYPE: PRT
<213> ORGANISM: Artificial Sequence
<220> FEATURE:
<223> OTHER INFORMATION: Targeting moiety

<400> SEQUENCE: 33

Ser Leu Asn Asp
1

<210> SEQ ID NO 34
<211> LENGTH: 4
<212> TYPE: PRT
<213> ORGANISM: Artificial Sequence
<220> FEATURE:
<223> OTHER INFORMATION: Targeting moiety

<400> SEQUENCE: 34

Ser Leu Asn Glu
1

<210> SEQ ID NO 35
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 35

Ser Leu Gln Asp
1

<210> SEQ ID NO 36
<211> LENGTH: 4
<212> TYPE: PRT
<213> ORGANISM: Artificial Sequence
<220> FEATURE:
<223> OTHER INFORMATION: Targeting moiety

<400> SEQUENCE: 36

Ser Leu Asp Glu
1

<210> SEQ ID NO 37
<211> LENGTH: 4
<212> TYPE: PRT
<213> ORGANISM: Artificial Sequence
<220> FEATURE:
<223> OTHER INFORMATION: Targeting moiety

<400> SEQUENCE: 37

Ser Met Ser Glu
1

<210> SEQ ID NO 38
<211> LENGTH: 4
<212> TYPE: PRT
<213> ORGANISM: Artificial Sequence
<220> FEATURE:
<223> OTHER INFORMATION: Targeting moiety

<400> SEQUENCE: 38

Ser Met Ser Asp
1

<210> SEQ ID NO 39
<211> LENGTH: 4
<212> TYPE: PRT
<213> ORGANISM: Artificial Sequence
<220> FEATURE:
<223> OTHER INFORMATION: Targeting moiety

<400> SEQUENCE: 39

Ser Met Cys Glu
1

<210> SEQ ID NO 40
<211> LENGTH: 4
<212> TYPE: PRT
<213> ORGANISM: Artificial Sequence
<220> FEATURE:
<223> OTHER INFORMATION: Targeting moiety

<400> SEQUENCE: 40

Ser Met Cys Asp
1

<210> SEQ ID NO 41
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 41

Ser Met Pro Asp
1

<210> SEQ ID NO 42
<211> LENGTH: 4
<212> TYPE: PRT
<213> ORGANISM: Artificial Sequence
<220> FEATURE:
<223> OTHER INFORMATION: Targeting moiety

<400> SEQUENCE: 42

Ser Met Pro Glu
1

<210> SEQ ID NO 43
<211> LENGTH: 4
<212> TYPE: PRT
<213> ORGANISM: Artificial Sequence
<220> FEATURE:
<223> OTHER INFORMATION: Targeting moiety

<400> SEQUENCE: 43

Ser Met Asn Asp
1

<210> SEQ ID NO 44
<211> LENGTH: 4
<212> TYPE: PRT
<213> ORGANISM: Artificial Sequence
<220> FEATURE:
<223> OTHER INFORMATION: Targeting moiety

<400> SEQUENCE: 44

Ser Met Asn Glu
1

<210> SEQ ID NO 45
<211> LENGTH: 4
<212> TYPE: PRT
<213> ORGANISM: Artificial Sequence
<220> FEATURE:
<223> OTHER INFORMATION: Targeting moiety

<400> SEQUENCE: 45

Ser Met Gln Asp
1

<210> SEQ ID NO 46
<211> LENGTH: 4
<212> TYPE: PRT
<213> ORGANISM: Artificial Sequence
<220> FEATURE:
<223> OTHER INFORMATION: Targeting moiety

<400> SEQUENCE: 46

Ser Met Gln Glu
1

<210> SEQ ID NO 47
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 47

Pro Ala Ser Asp
1

<210> SEQ ID NO 48
<211> LENGTH: 4
<212> TYPE: PRT
<213> ORGANISM: Artificial Sequence
<220> FEATURE:
<223> OTHER INFORMATION: Targeting moiety

<400> SEQUENCE: 48

Pro Ala Ser Glu
1

<210> SEQ ID NO 49
<211> LENGTH: 4
<212> TYPE: PRT
<213> ORGANISM: Artificial Sequence
<220> FEATURE:
<223> OTHER INFORMATION: Targeting moiety

<400> SEQUENCE: 49

Pro Ala Cys Asp
1

<210> SEQ ID NO 50
<211> LENGTH: 4
<212> TYPE: PRT
<213> ORGANISM: Artificial Sequence
<220> FEATURE:
<223> OTHER INFORMATION: Targeting moiety

<400> SEQUENCE: 50

Pro Ala Cys Glu
1

<210> SEQ ID NO 51
<211> LENGTH: 4
<212> TYPE: PRT
<213> ORGANISM: Artificial Sequence
<220> FEATURE:
<223> OTHER INFORMATION: Targeting moiety

<400> SEQUENCE: 51

Pro Ala Pro Asp
1

<210> SEQ ID NO 52
<211> LENGTH: 4
<212> TYPE: PRT
<213> ORGANISM: Artificial Sequence
<220> FEATURE:
<223> OTHER INFORMATION: Targeting moiety

<400> SEQUENCE: 52

Pro Ala Pro Glu
1

<210> SEQ ID NO 53
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 53

Pro Ala Asn Asp
1

<210> SEQ ID NO 54
<211> LENGTH: 4
<212> TYPE: PRT
<213> ORGANISM: Artificial Sequence
<220> FEATURE:
<223> OTHER INFORMATION: Targeting moiety

<400> SEQUENCE: 54

Pro Ala Asn Glu
1

<210> SEQ ID NO 55
<211> LENGTH: 4
<212> TYPE: PRT
<213> ORGANISM: Artificial Sequence
<220> FEATURE:
<223> OTHER INFORMATION: Targeting moiety

<400> SEQUENCE: 55

Pro Ala Gln Asp
1

<210> SEQ ID NO 56
<211> LENGTH: 4
<212> TYPE: PRT
<213> ORGANISM: Artificial Sequence
<220> FEATURE:
<223> OTHER INFORMATION: Targeting moiety

<400> SEQUENCE: 56

Pro Ala Gln Glu
1

<210> SEQ ID NO 57
<211> LENGTH: 4
<212> TYPE: PRT
<213> ORGANISM: Artificial Sequence
<220> FEATURE:
<223> OTHER INFORMATION: Targeting moiety

<400> SEQUENCE: 57

Pro Val Ser Asp
1

<210> SEQ ID NO 58
<211> LENGTH: 4
<212> TYPE: PRT
<213> ORGANISM: Artificial Sequence
<220> FEATURE:
<223> OTHER INFORMATION: Targeting moiety

<400> SEQUENCE: 58

Pro Val Ser Glu
1

<210> SEQ ID NO 59
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 59

Pro Val Cys Asp
1

<210> SEQ ID NO 60
<211> LENGTH: 4
<212> TYPE: PRT
<213> ORGANISM: Artificial Sequence
<220> FEATURE:
<223> OTHER INFORMATION: Targeting moiety

<400> SEQUENCE: 60

Pro Val Cys Glu
1

<210> SEQ ID NO 61
<211> LENGTH: 4
<212> TYPE: PRT
<213> ORGANISM: Artificial Sequence
<220> FEATURE:
<223> OTHER INFORMATION: Targeting moiety

<400> SEQUENCE: 61

Pro Val Pro Asp
1

<210> SEQ ID NO 62
<211> LENGTH: 4
<212> TYPE: PRT
<213> ORGANISM: Artificial Sequence
<220> FEATURE:
<223> OTHER INFORMATION: Targeting moiety

<400> SEQUENCE: 62

Pro Val Pro Glu
1

<210> SEQ ID NO 63
<211> LENGTH: 4
<212> TYPE: PRT
<213> ORGANISM: Artificial Sequence
<220> FEATURE:
<223> OTHER INFORMATION: Targeting moiety

<400> SEQUENCE: 63

Pro Val Asn Asp
1

<210> SEQ ID NO 64
<211> LENGTH: 4
<212> TYPE: PRT
<213> ORGANISM: Artificial Sequence
<220> FEATURE:
<223> OTHER INFORMATION: Targeting moiety

<400> SEQUENCE: 64

Pro Val Asn Glu
1

<210> SEQ ID NO 65
<211> LENGTH: 4
<212> TYPE: PRT
<213> ORGANISM: Artificial Sequence
<220> FEATURE:
<223> OTHER INFORMATION: Targeting moiety
```

<400> SEQUENCE: 65

Pro Val Gln Asp
1

<210> SEQ ID NO 66
<211> LENGTH: 4
<212> TYPE: PRT
<213> ORGANISM: Artificial Sequence
<220> FEATURE:
<223> OTHER INFORMATION: Targeting moiety

<400> SEQUENCE: 66

Pro Val Gln Glu
1

<210> SEQ ID NO 67
<211> LENGTH: 4
<212> TYPE: PRT
<213> ORGANISM: Artificial Sequence
<220> FEATURE:
<223> OTHER INFORMATION: Targeting moiety

<400> SEQUENCE: 67

Pro Leu Ser Asp
1

<210> SEQ ID NO 68
<211> LENGTH: 4
<212> TYPE: PRT
<213> ORGANISM: Artificial Sequence
<220> FEATURE:
<223> OTHER INFORMATION: Targeting moiety

<400> SEQUENCE: 68

Pro Leu Ser Glu
1

<210> SEQ ID NO 69
<211> LENGTH: 4
<212> TYPE: PRT
<213> ORGANISM: Artificial Sequence
<220> FEATURE:
<223> OTHER INFORMATION: Targeting moiety

<400> SEQUENCE: 69

Pro Leu Cys Asp
1

<210> SEQ ID NO 70
<211> LENGTH: 4
<212> TYPE: PRT
<213> ORGANISM: Artificial Sequence
<220> FEATURE:
<223> OTHER INFORMATION: Targeting moiety

<400> SEQUENCE: 70

Pro Leu Cys Glu
1

<210> SEQ ID NO 71
<211> LENGTH: 4
<212> TYPE: PRT
<213> ORGANISM: Artificial Sequence
<220> FEATURE:
<223> OTHER INFORMATION: Targeting moiety

```
<400> SEQUENCE: 71

Pro Leu Pro Asp
1

<210> SEQ ID NO 72
<211> LENGTH: 4
<212> TYPE: PRT
<213> ORGANISM: Artificial Sequence
<220> FEATURE:
<223> OTHER INFORMATION: Targeting moiety

<400> SEQUENCE: 72

Pro Leu Pro Glu
1

<210> SEQ ID NO 73
<211> LENGTH: 4
<212> TYPE: PRT
<213> ORGANISM: Artificial Sequence
<220> FEATURE:
<223> OTHER INFORMATION: Targeting moiety

<400> SEQUENCE: 73

Pro Leu Asn Asp
1

<210> SEQ ID NO 74
<211> LENGTH: 4
<212> TYPE: PRT
<213> ORGANISM: Artificial Sequence
<220> FEATURE:
<223> OTHER INFORMATION: Targeting moiety

<400> SEQUENCE: 74

Pro Leu Asn Glu
1

<210> SEQ ID NO 75
<211> LENGTH: 4
<212> TYPE: PRT
<213> ORGANISM: Artificial Sequence
<220> FEATURE:
<223> OTHER INFORMATION: Targeting moiety

<400> SEQUENCE: 75

Pro Leu Gln Asp
1

<210> SEQ ID NO 76
<211> LENGTH: 4
<212> TYPE: PRT
<213> ORGANISM: Artificial Sequence
<220> FEATURE:
<223> OTHER INFORMATION: Targeting moiety

<400> SEQUENCE: 76

Pro Leu Gln Glu
1

<210> SEQ ID NO 77
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 77

Pro Met Ser Asp
1

<210> SEQ ID NO 78
<211> LENGTH: 4
<212> TYPE: PRT
<213> ORGANISM: Artificial Sequence
<220> FEATURE:
<223> OTHER INFORMATION: Targeting moiety

<400> SEQUENCE: 78

Pro Met Ser Glu
1

<210> SEQ ID NO 79
<211> LENGTH: 4
<212> TYPE: PRT
<213> ORGANISM: Artificial Sequence
<220> FEATURE:
<223> OTHER INFORMATION: Targeting moiety

<400> SEQUENCE: 79

Pro Met Cys Asp
1

<210> SEQ ID NO 80
<211> LENGTH: 4
<212> TYPE: PRT
<213> ORGANISM: Artificial Sequence
<220> FEATURE:
<223> OTHER INFORMATION: Targeting moiety

<400> SEQUENCE: 80

Pro Met Cys Glu
1

<210> SEQ ID NO 81
<211> LENGTH: 4
<212> TYPE: PRT
<213> ORGANISM: Artificial Sequence
<220> FEATURE:
<223> OTHER INFORMATION: Targeting moiety

<400> SEQUENCE: 81

Cys Ala Ser Asp
1

<210> SEQ ID NO 82
<211> LENGTH: 4
<212> TYPE: PRT
<213> ORGANISM: Artificial Sequence
<220> FEATURE:
<223> OTHER INFORMATION: Targeting moiety

<400> SEQUENCE: 82

Cys Ala Ser Glu
1

<210> SEQ ID NO 83
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 83

Cys Ala Cys Asp
1

<210> SEQ ID NO 84
<211> LENGTH: 4
<212> TYPE: PRT
<213> ORGANISM: Artificial Sequence
<220> FEATURE:
<223> OTHER INFORMATION: Targeting moiety

<400> SEQUENCE: 84

Cys Ala Cys Glu
1

<210> SEQ ID NO 85
<211> LENGTH: 4
<212> TYPE: PRT
<213> ORGANISM: Artificial Sequence
<220> FEATURE:
<223> OTHER INFORMATION: Targeting moiety

<400> SEQUENCE: 85

Cys Ala Pro Asp
1

<210> SEQ ID NO 86
<211> LENGTH: 4
<212> TYPE: PRT
<213> ORGANISM: Artificial Sequence
<220> FEATURE:
<223> OTHER INFORMATION: Targeting moiety

<400> SEQUENCE: 86

Cys Ala Pro Glu
1

<210> SEQ ID NO 87
<211> LENGTH: 4
<212> TYPE: PRT
<213> ORGANISM: Artificial Sequence
<220> FEATURE:
<223> OTHER INFORMATION: Targeting moiety

<400> SEQUENCE: 87

Cys Ala Asn Asp
1

<210> SEQ ID NO 88
<211> LENGTH: 4
<212> TYPE: PRT
<213> ORGANISM: Artificial Sequence
<220> FEATURE:
<223> OTHER INFORMATION: Targeting moiety

<400> SEQUENCE: 88

Cys Ala Asn Glu
1

<210> SEQ ID NO 89
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 89

Cys Ala Gln Asp
1

<210> SEQ ID NO 90
<211> LENGTH: 4
<212> TYPE: PRT
<213> ORGANISM: Artificial Sequence
<220> FEATURE:
<223> OTHER INFORMATION: Targeting moiety

<400> SEQUENCE: 90

Cys Ala Gln Glu
1

<210> SEQ ID NO 91
<211> LENGTH: 4
<212> TYPE: PRT
<213> ORGANISM: Artificial Sequence
<220> FEATURE:
<223> OTHER INFORMATION: Targeting moiety

<400> SEQUENCE: 91

Cys Val Ser Asp
1

<210> SEQ ID NO 92
<211> LENGTH: 4
<212> TYPE: PRT
<213> ORGANISM: Artificial Sequence
<220> FEATURE:
<223> OTHER INFORMATION: Targeting moiety

<400> SEQUENCE: 92

Cys Val Ser Glu
1

<210> SEQ ID NO 93
<211> LENGTH: 4
<212> TYPE: PRT
<213> ORGANISM: Artificial Sequence
<220> FEATURE:
<223> OTHER INFORMATION: Targeting moiety

<400> SEQUENCE: 93

Cys Val Cys Asp
1

<210> SEQ ID NO 94
<211> LENGTH: 4
<212> TYPE: PRT
<213> ORGANISM: Artificial Sequence
<220> FEATURE:
<223> OTHER INFORMATION: Targeting moiety

<400> SEQUENCE: 94

Cys Val Cys Glu
1

<210> SEQ ID NO 95
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 95

Cys Val Pro Asp
1

<210> SEQ ID NO 96
<211> LENGTH: 4
<212> TYPE: PRT
<213> ORGANISM: Artificial Sequence
<220> FEATURE:
<223> OTHER INFORMATION: Targeting moiety

<400> SEQUENCE: 96

Cys Val Pro Glu
1

<210> SEQ ID NO 97
<211> LENGTH: 4
<212> TYPE: PRT
<213> ORGANISM: Artificial Sequence
<220> FEATURE:
<223> OTHER INFORMATION: Targeting moiety

<400> SEQUENCE: 97

Cys Val Asn Asp
1

<210> SEQ ID NO 98
<211> LENGTH: 4
<212> TYPE: PRT
<213> ORGANISM: Artificial Sequence
<220> FEATURE:
<223> OTHER INFORMATION: Targeting moiety

<400> SEQUENCE: 98

Cys Val Asn Glu
1

<210> SEQ ID NO 99
<211> LENGTH: 4
<212> TYPE: PRT
<213> ORGANISM: Artificial Sequence
<220> FEATURE:
<223> OTHER INFORMATION: Targeting moiety

<400> SEQUENCE: 99

Cys Val Gln Asp
1

<210> SEQ ID NO 100
<211> LENGTH: 4
<212> TYPE: PRT
<213> ORGANISM: Artificial Sequence
<220> FEATURE:
<223> OTHER INFORMATION: Targeting moiety

<400> SEQUENCE: 100

Cys Val Gln Glu
1

<210> SEQ ID NO 101
<211> LENGTH: 4
<212> TYPE: PRT
<213> ORGANISM: Artificial Sequence
<220> FEATURE:
<223> OTHER INFORMATION: Targeting moiety
```

<400> SEQUENCE: 101

Cys Leu Ser Asp
1

<210> SEQ ID NO 102
<211> LENGTH: 4
<212> TYPE: PRT
<213> ORGANISM: Artificial Sequence
<220> FEATURE:
<223> OTHER INFORMATION: Targeting moiety

<400> SEQUENCE: 102

Cys Leu Ser Glu
1

<210> SEQ ID NO 103
<211> LENGTH: 4
<212> TYPE: PRT
<213> ORGANISM: Artificial Sequence
<220> FEATURE:
<223> OTHER INFORMATION: Targeting moiety

<400> SEQUENCE: 103

Cys Leu Cys Asp
1

<210> SEQ ID NO 104
<211> LENGTH: 4
<212> TYPE: PRT
<213> ORGANISM: Artificial Sequence
<220> FEATURE:
<223> OTHER INFORMATION: Targeting moiety

<400> SEQUENCE: 104

Cys Leu Cys Glu
1

<210> SEQ ID NO 105
<211> LENGTH: 4
<212> TYPE: PRT
<213> ORGANISM: Artificial Sequence
<220> FEATURE:
<223> OTHER INFORMATION: Targeting moiety

<400> SEQUENCE: 105

Cys Leu Pro Asp
1

<210> SEQ ID NO 106
<211> LENGTH: 4
<212> TYPE: PRT
<213> ORGANISM: Artificial Sequence
<220> FEATURE:
<223> OTHER INFORMATION: Targeting moiety

<400> SEQUENCE: 106

Cys Leu Pro Glu
1

<210> SEQ ID NO 107
<211> LENGTH: 4
<212> TYPE: PRT
<213> ORGANISM: Artificial Sequence
<220> FEATURE:
<223> OTHER INFORMATION: Targeting moiety

```
<400> SEQUENCE: 107

Cys Leu Asn Asp
1

<210> SEQ ID NO 108
<211> LENGTH: 4
<212> TYPE: PRT
<213> ORGANISM: Artificial Sequence
<220> FEATURE:
<223> OTHER INFORMATION: Targeting moiety

<400> SEQUENCE: 108

Cys Leu Asn Glu
1

<210> SEQ ID NO 109
<211> LENGTH: 4
<212> TYPE: PRT
<213> ORGANISM: Artificial Sequence
<220> FEATURE:
<223> OTHER INFORMATION: Targeting moiety

<400> SEQUENCE: 109

Cys Leu Gln Asp
1

<210> SEQ ID NO 110
<211> LENGTH: 4
<212> TYPE: PRT
<213> ORGANISM: Artificial Sequence
<220> FEATURE:
<223> OTHER INFORMATION: Targeting moiety

<400> SEQUENCE: 110

Cys Leu Gln Glu
1

<210> SEQ ID NO 111
<211> LENGTH: 4
<212> TYPE: PRT
<213> ORGANISM: Artificial Sequence
<220> FEATURE:
<223> OTHER INFORMATION: Targeting moiety

<400> SEQUENCE: 111

Cys Met Ser Asp
1

<210> SEQ ID NO 112
<211> LENGTH: 4
<212> TYPE: PRT
<213> ORGANISM: Artificial Sequence
<220> FEATURE:
<223> OTHER INFORMATION: Targeting moiety

<400> SEQUENCE: 112

Cys Met Ser Glu
1

<210> SEQ ID NO 113
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 113

Cys Met Cys Asp
1

<210> SEQ ID NO 114
<211> LENGTH: 4
<212> TYPE: PRT
<213> ORGANISM: Artificial Sequence
<220> FEATURE:
<223> OTHER INFORMATION: Targeting moiety

<400> SEQUENCE: 114

Cys Met Ser Glu
1

<210> SEQ ID NO 115
<211> LENGTH: 4
<212> TYPE: PRT
<213> ORGANISM: Artificial Sequence
<220> FEATURE:
<223> OTHER INFORMATION: Targeting moiety

<400> SEQUENCE: 115

Cys Met Pro Asp
1

<210> SEQ ID NO 116
<211> LENGTH: 4
<212> TYPE: PRT
<213> ORGANISM: Artificial Sequence
<220> FEATURE:
<223> OTHER INFORMATION: Targeting moiety

<400> SEQUENCE: 116

Cys Met Pro Glu
1

<210> SEQ ID NO 117
<211> LENGTH: 4
<212> TYPE: PRT
<213> ORGANISM: Artificial Sequence
<220> FEATURE:
<223> OTHER INFORMATION: Targeting moiety

<400> SEQUENCE: 117

Cys Met Asn Asp
1

<210> SEQ ID NO 118
<211> LENGTH: 4
<212> TYPE: PRT
<213> ORGANISM: Artificial Sequence
<220> FEATURE:
<223> OTHER INFORMATION: Targeting moiety

<400> SEQUENCE: 118

Cys Met Asn Glu
1

<210> SEQ ID NO 119
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 119

Cys Met Gln Asp
1

<210> SEQ ID NO 120
<211> LENGTH: 4
<212> TYPE: PRT
<213> ORGANISM: Artificial Sequence
<220> FEATURE:
<223> OTHER INFORMATION: Targeting moiety

<400> SEQUENCE: 120

Cys Met Gln Glu
1

<210> SEQ ID NO 121
<211> LENGTH: 4
<212> TYPE: PRT
<213> ORGANISM: Artificial Sequence
<220> FEATURE:
<223> OTHER INFORMATION: Targeting moiety

<400> SEQUENCE: 121

Thr Ala Ser Asp
1

<210> SEQ ID NO 122
<211> LENGTH: 4
<212> TYPE: PRT
<213> ORGANISM: Artificial Sequence
<220> FEATURE:
<223> OTHER INFORMATION: Targeting moiety

<400> SEQUENCE: 122

Thr Ala Ser Glu
1

<210> SEQ ID NO 123
<211> LENGTH: 4
<212> TYPE: PRT
<213> ORGANISM: Artificial Sequence
<220> FEATURE:
<223> OTHER INFORMATION: Targeting moiety

<400> SEQUENCE: 123

Thr Ala Cys Asp
1

<210> SEQ ID NO 124
<211> LENGTH: 4
<212> TYPE: PRT
<213> ORGANISM: Artificial Sequence
<220> FEATURE:
<223> OTHER INFORMATION: Targeting moiety

<400> SEQUENCE: 124

Thr Ala Cys Glu
1

<210> SEQ ID NO 125
<211> LENGTH: 4
<212> TYPE: PRT
<213> ORGANISM: Artificial Sequence
<220> FEATURE:
<223> OTHER INFORMATION: Targeting moiety
```

<400> SEQUENCE: 125

Thr Ala Pro Asp
1

<210> SEQ ID NO 126
<211> LENGTH: 4
<212> TYPE: PRT
<213> ORGANISM: Artificial Sequence
<220> FEATURE:
<223> OTHER INFORMATION: Targeting moiety

<400> SEQUENCE: 126

Thr Ala Pro Glu
1

<210> SEQ ID NO 127
<211> LENGTH: 4
<212> TYPE: PRT
<213> ORGANISM: Artificial Sequence
<220> FEATURE:
<223> OTHER INFORMATION: Targeting moiety

<400> SEQUENCE: 127

Thr Ala Asn Asp
1

<210> SEQ ID NO 128
<211> LENGTH: 4
<212> TYPE: PRT
<213> ORGANISM: Artificial Sequence
<220> FEATURE:
<223> OTHER INFORMATION: Targeting moiety

<400> SEQUENCE: 128

Thr Ala Asn Glu
1

<210> SEQ ID NO 129
<211> LENGTH: 4
<212> TYPE: PRT
<213> ORGANISM: Artificial Sequence
<220> FEATURE:
<223> OTHER INFORMATION: Targeting moiety

<400> SEQUENCE: 129

Thr Ala Gln Asp
1

<210> SEQ ID NO 130
<211> LENGTH: 4
<212> TYPE: PRT
<213> ORGANISM: Artificial Sequence
<220> FEATURE:
<223> OTHER INFORMATION: Targeting moiety

<400> SEQUENCE: 130

Thr Ala Gln Glu
1

<210> SEQ ID NO 131
<211> LENGTH: 4
<212> TYPE: PRT
<213> ORGANISM: Artificial Sequence
<220> FEATURE:
<223> OTHER INFORMATION: Targeting moiety

```
<400> SEQUENCE: 131

Thr Val Ser Asp
1

<210> SEQ ID NO 132
<211> LENGTH: 4
<212> TYPE: PRT
<213> ORGANISM: Artificial Sequence
<220> FEATURE:
<223> OTHER INFORMATION: Targeting moiety

<400> SEQUENCE: 132

Thr Val Ser Glu
1

<210> SEQ ID NO 133
<211> LENGTH: 4
<212> TYPE: PRT
<213> ORGANISM: Artificial Sequence
<220> FEATURE:
<223> OTHER INFORMATION: Targeting moiety

<400> SEQUENCE: 133

Thr Val Cys Asp
1

<210> SEQ ID NO 134
<211> LENGTH: 4
<212> TYPE: PRT
<213> ORGANISM: Artificial Sequence
<220> FEATURE:
<223> OTHER INFORMATION: Targeting moiety

<400> SEQUENCE: 134

Thr Val Cys Glu
1

<210> SEQ ID NO 135
<211> LENGTH: 4
<212> TYPE: PRT
<213> ORGANISM: Artificial Sequence
<220> FEATURE:
<223> OTHER INFORMATION: Targeting moiety

<400> SEQUENCE: 135

Thr Val Pro Asp
1

<210> SEQ ID NO 136
<211> LENGTH: 4
<212> TYPE: PRT
<213> ORGANISM: Artificial Sequence
<220> FEATURE:
<223> OTHER INFORMATION: Targeting moiety

<400> SEQUENCE: 136

Thr Val Pro Glu
1

<210> SEQ ID NO 137
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 137

Thr Val Asn Asp
1

<210> SEQ ID NO 138
<211> LENGTH: 4
<212> TYPE: PRT
<213> ORGANISM: Artificial Sequence
<220> FEATURE:
<223> OTHER INFORMATION: Targeting moiety

<400> SEQUENCE: 138

Thr Val Asn Glu
1

<210> SEQ ID NO 139
<211> LENGTH: 4
<212> TYPE: PRT
<213> ORGANISM: Artificial Sequence
<220> FEATURE:
<223> OTHER INFORMATION: Targeting moiety

<400> SEQUENCE: 139

Thr Val Gln Asp
1

<210> SEQ ID NO 140
<211> LENGTH: 4
<212> TYPE: PRT
<213> ORGANISM: Artificial Sequence
<220> FEATURE:
<223> OTHER INFORMATION: Targeting moiety

<400> SEQUENCE: 140

Thr Val Gln Glu
1

<210> SEQ ID NO 141
<211> LENGTH: 4
<212> TYPE: PRT
<213> ORGANISM: Artificial Sequence
<220> FEATURE:
<223> OTHER INFORMATION: Targeting moiety

<400> SEQUENCE: 141

Thr Leu Ser Asp
1

<210> SEQ ID NO 142
<211> LENGTH: 4
<212> TYPE: PRT
<213> ORGANISM: Artificial Sequence
<220> FEATURE:
<223> OTHER INFORMATION: Targeting moiety

<400> SEQUENCE: 142

Thr Leu Ser Glu
1

<210> SEQ ID NO 143
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 143

Thr Leu Cys Asp
1

<210> SEQ ID NO 144
<211> LENGTH: 4
<212> TYPE: PRT
<213> ORGANISM: Artificial Sequence
<220> FEATURE:
<223> OTHER INFORMATION: Targeting moiety

<400> SEQUENCE: 144

Thr Leu Cys Glu
1

<210> SEQ ID NO 145
<211> LENGTH: 4
<212> TYPE: PRT
<213> ORGANISM: Artificial Sequence
<220> FEATURE:
<223> OTHER INFORMATION: Targeting moiety

<400> SEQUENCE: 145

Thr Leu Pro Asp
1

<210> SEQ ID NO 146
<211> LENGTH: 4
<212> TYPE: PRT
<213> ORGANISM: Artificial Sequence
<220> FEATURE:
<223> OTHER INFORMATION: Targeting moiety

<400> SEQUENCE: 146

Thr Leu Pro Glu
1

<210> SEQ ID NO 147
<211> LENGTH: 4
<212> TYPE: PRT
<213> ORGANISM: Artificial Sequence
<220> FEATURE:
<223> OTHER INFORMATION: Targeting moiety

<400> SEQUENCE: 147

Thr Leu Asn Asp
1

<210> SEQ ID NO 148
<211> LENGTH: 4
<212> TYPE: PRT
<213> ORGANISM: Artificial Sequence
<220> FEATURE:
<223> OTHER INFORMATION: Targeting moiety

<400> SEQUENCE: 148

Thr Leu Asn Glu
1

<210> SEQ ID NO 149
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 149

Thr Leu Gln Asp
1

<210> SEQ ID NO 150
<211> LENGTH: 4
<212> TYPE: PRT
<213> ORGANISM: Artificial Sequence
<220> FEATURE:
<223> OTHER INFORMATION: Targeting moiety

<400> SEQUENCE: 150

Thr Leu Gln Glu
1

<210> SEQ ID NO 151
<211> LENGTH: 4
<212> TYPE: PRT
<213> ORGANISM: Artificial Sequence
<220> FEATURE:
<223> OTHER INFORMATION: Targeting moiety

<400> SEQUENCE: 151

Thr Met Ser Asp
1

<210> SEQ ID NO 152
<211> LENGTH: 4
<212> TYPE: PRT
<213> ORGANISM: Artificial Sequence
<220> FEATURE:
<223> OTHER INFORMATION: Targeting moiety

<400> SEQUENCE: 152

Thr Met Ser Glu
1

<210> SEQ ID NO 153
<211> LENGTH: 4
<212> TYPE: PRT
<213> ORGANISM: Artificial Sequence
<220> FEATURE:
<223> OTHER INFORMATION: Targeting moiety

<400> SEQUENCE: 153

Thr Met Cys Asp
1

<210> SEQ ID NO 154
<211> LENGTH: 4
<212> TYPE: PRT
<213> ORGANISM: Artificial Sequence
<220> FEATURE:
<223> OTHER INFORMATION: Targeting moiety

<400> SEQUENCE: 154

Thr Met Cys Glu
1

<210> SEQ ID NO 155
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 155

Thr Met Pro Asp
1

<210> SEQ ID NO 156
<211> LENGTH: 4
<212> TYPE: PRT
<213> ORGANISM: Artificial Sequence
<220> FEATURE:
<223> OTHER INFORMATION: Targeting moiety

<400> SEQUENCE: 156

Thr Met Pro Glu
1

<210> SEQ ID NO 157
<211> LENGTH: 4
<212> TYPE: PRT
<213> ORGANISM: Artificial Sequence
<220> FEATURE:
<223> OTHER INFORMATION: Targeting moiety

<400> SEQUENCE: 157

Thr Met Asn Asp
1

<210> SEQ ID NO 158
<211> LENGTH: 4
<212> TYPE: PRT
<213> ORGANISM: Artificial Sequence
<220> FEATURE:
<223> OTHER INFORMATION: Targeting moiety

<400> SEQUENCE: 158

Thr Met Asn Glu
1

<210> SEQ ID NO 159
<211> LENGTH: 4
<212> TYPE: PRT
<213> ORGANISM: Artificial Sequence
<220> FEATURE:
<223> OTHER INFORMATION: Targeting moiety

<400> SEQUENCE: 159

Thr Met Gln Asp
1

<210> SEQ ID NO 160
<211> LENGTH: 4
<212> TYPE: PRT
<213> ORGANISM: Artificial Sequence
<220> FEATURE:
<223> OTHER INFORMATION: Targeting moiety

<400> SEQUENCE: 160

Thr Met Gln Glu
1

<210> SEQ ID NO 161
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 161

Gln Ala Ser Asp
1

<210> SEQ ID NO 162
<211> LENGTH: 4
<212> TYPE: PRT
<213> ORGANISM: Artificial Sequence
<220> FEATURE:
<223> OTHER INFORMATION: Targeting moiety

<400> SEQUENCE: 162

Gln Ala Ser Glu
1

<210> SEQ ID NO 163
<211> LENGTH: 4
<212> TYPE: PRT
<213> ORGANISM: Artificial Sequence
<220> FEATURE:
<223> OTHER INFORMATION: Targeting moiety

<400> SEQUENCE: 163

Gln Val Cys Asp
1

<210> SEQ ID NO 164
<211> LENGTH: 4
<212> TYPE: PRT
<213> ORGANISM: Artificial Sequence
<220> FEATURE:
<223> OTHER INFORMATION: Targeting moiety

<400> SEQUENCE: 164

Gln Val Cys Glu
1

<210> SEQ ID NO 165
<211> LENGTH: 4
<212> TYPE: PRT
<213> ORGANISM: Artificial Sequence
<220> FEATURE:
<223> OTHER INFORMATION: Targeting moiety

<400> SEQUENCE: 165

Gln Val Pro Asp
1

<210> SEQ ID NO 166
<211> LENGTH: 4
<212> TYPE: PRT
<213> ORGANISM: Artificial Sequence
<220> FEATURE:
<223> OTHER INFORMATION: Targeting moiety

<400> SEQUENCE: 166

Gln Val Pro Glu
1

<210> SEQ ID NO 167
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 167

Gln Val Asn Asp
1

<210> SEQ ID NO 168
<211> LENGTH: 4
<212> TYPE: PRT
<213> ORGANISM: Artificial Sequence
<220> FEATURE:
<223> OTHER INFORMATION: Targeting moiety

<400> SEQUENCE: 168

Gln Val Asn Glu
1

<210> SEQ ID NO 169
<211> LENGTH: 4
<212> TYPE: PRT
<213> ORGANISM: Artificial Sequence
<220> FEATURE:
<223> OTHER INFORMATION: Targeting moiety

<400> SEQUENCE: 169

Gln Val Gln Asp
1

<210> SEQ ID NO 170
<211> LENGTH: 4
<212> TYPE: PRT
<213> ORGANISM: Artificial Sequence
<220> FEATURE:
<223> OTHER INFORMATION: Targeting moiety

<400> SEQUENCE: 170

Gln Val Gln Glu
1

<210> SEQ ID NO 171
<211> LENGTH: 4
<212> TYPE: PRT
<213> ORGANISM: Artificial Sequence
<220> FEATURE:
<223> OTHER INFORMATION: Targeting moiety

<400> SEQUENCE: 171

Gln Leu Ser Asp
1

<210> SEQ ID NO 172
<211> LENGTH: 4
<212> TYPE: PRT
<213> ORGANISM: Artificial Sequence
<220> FEATURE:
<223> OTHER INFORMATION: Targeting moiety

<400> SEQUENCE: 172

Gln Leu Ser Glu
1

<210> SEQ ID NO 173
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 173

Gln Leu Cys Asp
1

<210> SEQ ID NO 174
<211> LENGTH: 4
<212> TYPE: PRT
<213> ORGANISM: Artificial Sequence
<220> FEATURE:
<223> OTHER INFORMATION: Targeting moiety

<400> SEQUENCE: 174

Gln Leu Cys Glu
1

<210> SEQ ID NO 175
<211> LENGTH: 4
<212> TYPE: PRT
<213> ORGANISM: Artificial Sequence
<220> FEATURE:
<223> OTHER INFORMATION: Targeting moiety

<400> SEQUENCE: 175

Gln Leu Pro Asp
1

<210> SEQ ID NO 176
<211> LENGTH: 4
<212> TYPE: PRT
<213> ORGANISM: Artificial Sequence
<220> FEATURE:
<223> OTHER INFORMATION: Targeting moiety

<400> SEQUENCE: 176

Gln Leu Pro Glu
1

<210> SEQ ID NO 177
<211> LENGTH: 4
<212> TYPE: PRT
<213> ORGANISM: Artificial Sequence
<220> FEATURE:
<223> OTHER INFORMATION: Targeting moiety

<400> SEQUENCE: 177

Gln Leu Asn Asp
1

<210> SEQ ID NO 178
<211> LENGTH: 4
<212> TYPE: PRT
<213> ORGANISM: Artificial Sequence
<220> FEATURE:
<223> OTHER INFORMATION: Targeting moiety

<400> SEQUENCE: 178

Gln Leu Asn Glu
1

<210> SEQ ID NO 179
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 179

Gln Leu Gln Asp
1

<210> SEQ ID NO 180
<211> LENGTH: 4
<212> TYPE: PRT
<213> ORGANISM: Artificial Sequence
<220> FEATURE:
<223> OTHER INFORMATION: Targeting moiety

<400> SEQUENCE: 180

Gln Leu Gln Glu
1

<210> SEQ ID NO 181
<211> LENGTH: 4
<212> TYPE: PRT
<213> ORGANISM: Artificial Sequence
<220> FEATURE:
<223> OTHER INFORMATION: Targeting moiety

<400> SEQUENCE: 181

Gln Met Ser Asp
1

<210> SEQ ID NO 182
<211> LENGTH: 4
<212> TYPE: PRT
<213> ORGANISM: Artificial Sequence
<220> FEATURE:
<223> OTHER INFORMATION: Targeting moiety

<400> SEQUENCE: 182

Gln Met Ser Glu
1

<210> SEQ ID NO 183
<211> LENGTH: 4
<212> TYPE: PRT
<213> ORGANISM: Artificial Sequence
<220> FEATURE:
<223> OTHER INFORMATION: Targeting moiety

<400> SEQUENCE: 183

Gln Met Cys Asp
1

<210> SEQ ID NO 184
<211> LENGTH: 4
<212> TYPE: PRT
<213> ORGANISM: Artificial Sequence
<220> FEATURE:
<223> OTHER INFORMATION: Targeting moiety

<400> SEQUENCE: 184

Gln Met Cys Glu
1

<210> SEQ ID NO 185
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 185

Gln Met Pro Asp
1

<210> SEQ ID NO 186
<211> LENGTH: 4
<212> TYPE: PRT
<213> ORGANISM: Artificial Sequence
<220> FEATURE:
<223> OTHER INFORMATION: Targeting moiety

<400> SEQUENCE: 186

Gln Met Pro Glu
1

<210> SEQ ID NO 187
<211> LENGTH: 4
<212> TYPE: PRT
<213> ORGANISM: Artificial Sequence
<220> FEATURE:
<223> OTHER INFORMATION: Targeting moiety

<400> SEQUENCE: 187

Gln Met Asn Asp
1

<210> SEQ ID NO 188
<211> LENGTH: 4
<212> TYPE: PRT
<213> ORGANISM: Artificial Sequence
<220> FEATURE:
<223> OTHER INFORMATION: Targeting moiety

<400> SEQUENCE: 188

Gln Met Asn Glu
1

<210> SEQ ID NO 189
<211> LENGTH: 4
<212> TYPE: PRT
<213> ORGANISM: Artificial Sequence
<220> FEATURE:
<223> OTHER INFORMATION: Targeting moiety

<400> SEQUENCE: 189

Gln Met Gln Asp
1

<210> SEQ ID NO 190
<211> LENGTH: 4
<212> TYPE: PRT
<213> ORGANISM: Artificial Sequence
<220> FEATURE:
<223> OTHER INFORMATION: Targeting moiety

<400> SEQUENCE: 190

Gln Met Gln Glu
1

<210> SEQ ID NO 191
<211> LENGTH: 4
<212> TYPE: PRT
<213> ORGANISM: Artificial Sequence
<220> FEATURE:
<223> OTHER INFORMATION: Targeting moiety
```

<400> SEQUENCE: 191

Met Ile His Ser
1

<210> SEQ ID NO 192
<211> LENGTH: 4
<212> TYPE: PRT
<213> ORGANISM: Artificial Sequence
<220> FEATURE:
<223> OTHER INFORMATION: Targeting moiety

<400> SEQUENCE: 192

Ala Ile His Ser
1

<210> SEQ ID NO 193
<211> LENGTH: 4
<212> TYPE: PRT
<213> ORGANISM: Artificial Sequence
<220> FEATURE:
<223> OTHER INFORMATION: Targeting moiety

<400> SEQUENCE: 193

Val Ile His Ser
1

<210> SEQ ID NO 194
<211> LENGTH: 4
<212> TYPE: PRT
<213> ORGANISM: Artificial Sequence
<220> FEATURE:
<223> OTHER INFORMATION: Targeting moiety

<400> SEQUENCE: 194

Ile Ile His Ser
1

<210> SEQ ID NO 195
<211> LENGTH: 4
<212> TYPE: PRT
<213> ORGANISM: Artificial Sequence
<220> FEATURE:
<223> OTHER INFORMATION: Targeting moiety

<400> SEQUENCE: 195

Leu Ile His Ser
1

<210> SEQ ID NO 196
<211> LENGTH: 4
<212> TYPE: PRT
<213> ORGANISM: Artificial Sequence
<220> FEATURE:
<223> OTHER INFORMATION: Targeting moiety

<400> SEQUENCE: 196

Phe Ile His Ser
1

<210> SEQ ID NO 197
<211> LENGTH: 4
<212> TYPE: PRT
<213> ORGANISM: Artificial Sequence
<220> FEATURE:
<223> OTHER INFORMATION: Targeting moiety

```
<400> SEQUENCE: 197

Tyr Ile His Ser
1

<210> SEQ ID NO 198
<211> LENGTH: 4
<212> TYPE: PRT
<213> ORGANISM: Artificial Sequence
<220> FEATURE:
<223> OTHER INFORMATION: Targeting moiety

<400> SEQUENCE: 198

Trp Ile His Ser
1

<210> SEQ ID NO 199
<211> LENGTH: 4
<212> TYPE: PRT
<213> ORGANISM: Artificial Sequence
<220> FEATURE:
<223> OTHER INFORMATION: Targeting moiety

<400> SEQUENCE: 199

Met Ala His Ser
1

<210> SEQ ID NO 200
<211> LENGTH: 4
<212> TYPE: PRT
<213> ORGANISM: Artificial Sequence
<220> FEATURE:
<223> OTHER INFORMATION: Targeting moiety

<400> SEQUENCE: 200

Met Val His Ser
1

<210> SEQ ID NO 201
<211> LENGTH: 4
<212> TYPE: PRT
<213> ORGANISM: Artificial Sequence
<220> FEATURE:
<223> OTHER INFORMATION: Targeting moiety

<400> SEQUENCE: 201

Met Leu His Ser
1

<210> SEQ ID NO 202
<211> LENGTH: 4
<212> TYPE: PRT
<213> ORGANISM: Artificial Sequence
<220> FEATURE:
<223> OTHER INFORMATION: Targeting moiety

<400> SEQUENCE: 202

Met Met His Ser
1

<210> SEQ ID NO 203
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 203

Met Phe His Ser
1

<210> SEQ ID NO 204
<211> LENGTH: 4
<212> TYPE: PRT
<213> ORGANISM: Artificial Sequence
<220> FEATURE:
<223> OTHER INFORMATION: Targeting moiety

<400> SEQUENCE: 204

Met Tyr His Ser
1

<210> SEQ ID NO 205
<211> LENGTH: 4
<212> TYPE: PRT
<213> ORGANISM: Artificial Sequence
<220> FEATURE:
<223> OTHER INFORMATION: Targeting moiety

<400> SEQUENCE: 205

Met Trp His Ser
1

<210> SEQ ID NO 206
<211> LENGTH: 4
<212> TYPE: PRT
<213> ORGANISM: Artificial Sequence
<220> FEATURE:
<223> OTHER INFORMATION: Targeting moiety

<400> SEQUENCE: 206

Ala Ile Arg Ser
1

<210> SEQ ID NO 207
<211> LENGTH: 4
<212> TYPE: PRT
<213> ORGANISM: Artificial Sequence
<220> FEATURE:
<223> OTHER INFORMATION: Targeting moiety

<400> SEQUENCE: 207

Ala Ile Arg Lys
1

<210> SEQ ID NO 208
<211> LENGTH: 4
<212> TYPE: PRT
<213> ORGANISM: Artificial Sequence
<220> FEATURE:
<223> OTHER INFORMATION: Targeting moiety

<400> SEQUENCE: 208

Ala Ile Asp Lys
1

<210> SEQ ID NO 209
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 209

Ala Ile Glu Lys
1

<210> SEQ ID NO 210
<211> LENGTH: 4
<212> TYPE: PRT
<213> ORGANISM: Artificial Sequence
<220> FEATURE:
<223> OTHER INFORMATION: Targeting moiety

<400> SEQUENCE: 210

Met Ile His Thr
1

<210> SEQ ID NO 211
<211> LENGTH: 4
<212> TYPE: PRT
<213> ORGANISM: Artificial Sequence
<220> FEATURE:
<223> OTHER INFORMATION: Targeting moiety

<400> SEQUENCE: 211

Met Ile His Asn
1

<210> SEQ ID NO 212
<211> LENGTH: 4
<212> TYPE: PRT
<213> ORGANISM: Artificial Sequence
<220> FEATURE:
<223> OTHER INFORMATION: Targeting moiety

<400> SEQUENCE: 212

Met Ile His Gln
1

<210> SEQ ID NO 213
<211> LENGTH: 4
<212> TYPE: PRT
<213> ORGANISM: Artificial Sequence
<220> FEATURE:
<223> OTHER INFORMATION: Targeting moiety

<400> SEQUENCE: 213

Ala Ser Cys Ser
1

<210> SEQ ID NO 214
<211> LENGTH: 4
<212> TYPE: PRT
<213> ORGANISM: Artificial Sequence
<220> FEATURE:
<223> OTHER INFORMATION: Targeting moiety

<400> SEQUENCE: 214

Ala Thr Cys Ser
1

<210> SEQ ID NO 215
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 215

Ala Asn Cys Ser
1

<210> SEQ ID NO 216
<211> LENGTH: 4
<212> TYPE: PRT
<213> ORGANISM: Artificial Sequence
<220> FEATURE:
<223> OTHER INFORMATION: Targeting moiety

<400> SEQUENCE: 216

Ala Gln Cys Ser
1

<210> SEQ ID NO 217
<211> LENGTH: 4
<212> TYPE: PRT
<213> ORGANISM: Artificial Sequence
<220> FEATURE:
<223> OTHER INFORMATION: Targeting moiety

<400> SEQUENCE: 217

Ala Val Cys Ser
1

<210> SEQ ID NO 218
<211> LENGTH: 4
<212> TYPE: PRT
<213> ORGANISM: Artificial Sequence
<220> FEATURE:
<223> OTHER INFORMATION: Targeting moiety

<400> SEQUENCE: 218

Val Ser Cys Ser
1

<210> SEQ ID NO 219
<211> LENGTH: 4
<212> TYPE: PRT
<213> ORGANISM: Artificial Sequence
<220> FEATURE:
<223> OTHER INFORMATION: Targeting moiety

<400> SEQUENCE: 219

Val Thr Cys Ser
1

<210> SEQ ID NO 220
<211> LENGTH: 4
<212> TYPE: PRT
<213> ORGANISM: Artificial Sequence
<220> FEATURE:
<223> OTHER INFORMATION: Targeting moiety

<400> SEQUENCE: 220

Val Asn Cys Ser
1

<210> SEQ ID NO 221
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 221

Val Gln Cys Ser
1

<210> SEQ ID NO 222
<211> LENGTH: 4
<212> TYPE: PRT
<213> ORGANISM: Artificial Sequence
<220> FEATURE:
<223> OTHER INFORMATION: Targeting moiety

<400> SEQUENCE: 222

Val Val Cys Ser
1

<210> SEQ ID NO 223
<211> LENGTH: 4
<212> TYPE: PRT
<213> ORGANISM: Artificial Sequence
<220> FEATURE:
<223> OTHER INFORMATION: Targeting moiety

<400> SEQUENCE: 223

Ile Ser Cys Ser
1

<210> SEQ ID NO 224
<211> LENGTH: 4
<212> TYPE: PRT
<213> ORGANISM: Artificial Sequence
<220> FEATURE:
<223> OTHER INFORMATION: Targeting moiety

<400> SEQUENCE: 224

Ile Thr Cys Ser
1

<210> SEQ ID NO 225
<211> LENGTH: 4
<212> TYPE: PRT
<213> ORGANISM: Artificial Sequence
<220> FEATURE:
<223> OTHER INFORMATION: Targeting moiety

<400> SEQUENCE: 225

Ile Asn Cys Ser
1

<210> SEQ ID NO 226
<211> LENGTH: 4
<212> TYPE: PRT
<213> ORGANISM: Artificial Sequence
<220> FEATURE:
<223> OTHER INFORMATION: Targeting moiety

<400> SEQUENCE: 226

Ile Gln Cys Ser
1

<210> SEQ ID NO 227
<211> LENGTH: 4
<212> TYPE: PRT
<213> ORGANISM: Artificial Sequence
<220> FEATURE:
<223> OTHER INFORMATION: Targeting moiety
```

<400> SEQUENCE: 227

Ile Val Cys Ser
1

<210> SEQ ID NO 228
<211> LENGTH: 4
<212> TYPE: PRT
<213> ORGANISM: Artificial Sequence
<220> FEATURE:
<223> OTHER INFORMATION: Targeting moiety

<400> SEQUENCE: 228

Leu Ser Cys Ser
1

<210> SEQ ID NO 229
<211> LENGTH: 4
<212> TYPE: PRT
<213> ORGANISM: Artificial Sequence
<220> FEATURE:
<223> OTHER INFORMATION: Targeting moiety

<400> SEQUENCE: 229

Leu Thr Cys Ser
1

<210> SEQ ID NO 230
<211> LENGTH: 4
<212> TYPE: PRT
<213> ORGANISM: Artificial Sequence
<220> FEATURE:
<223> OTHER INFORMATION: Targeting moiety

<400> SEQUENCE: 230

Leu Asn Cys Ser
1

<210> SEQ ID NO 231
<211> LENGTH: 4
<212> TYPE: PRT
<213> ORGANISM: Artificial Sequence
<220> FEATURE:
<223> OTHER INFORMATION: Targeting moiety

<400> SEQUENCE: 231

Leu Gln Cys Ser
1

<210> SEQ ID NO 232
<211> LENGTH: 4
<212> TYPE: PRT
<213> ORGANISM: Artificial Sequence
<220> FEATURE:
<223> OTHER INFORMATION: Targeting moiety

<400> SEQUENCE: 232

Met Ser Cys Ser
1

<210> SEQ ID NO 233
<211> LENGTH: 4
<212> TYPE: PRT
<213> ORGANISM: Artificial Sequence
<220> FEATURE:
<223> OTHER INFORMATION: Targeting moiety

<400> SEQUENCE: 233

Met Thr Cys Ser
1

<210> SEQ ID NO 234
<211> LENGTH: 4
<212> TYPE: PRT
<213> ORGANISM: Artificial Sequence
<220> FEATURE:
<223> OTHER INFORMATION: Targeting moiety

<400> SEQUENCE: 234

Met Asn Cys Ser
1

<210> SEQ ID NO 235
<211> LENGTH: 4
<212> TYPE: PRT
<213> ORGANISM: Artificial Sequence
<220> FEATURE:
<223> OTHER INFORMATION: Targeting moiety

<400> SEQUENCE: 235

Met Gln Cys Ser
1

<210> SEQ ID NO 236
<211> LENGTH: 4
<212> TYPE: PRT
<213> ORGANISM: Artificial Sequence
<220> FEATURE:
<223> OTHER INFORMATION: Targeting moiety

<400> SEQUENCE: 236

Met Val Cys Ser
1

<210> SEQ ID NO 237
<211> LENGTH: 4
<212> TYPE: PRT
<213> ORGANISM: Artificial Sequence
<220> FEATURE:
<223> OTHER INFORMATION: Targeting moiety

<400> SEQUENCE: 237

Phe Ser Cys Ser
1

<210> SEQ ID NO 238
<211> LENGTH: 4
<212> TYPE: PRT
<213> ORGANISM: Artificial Sequence
<220> FEATURE:
<223> OTHER INFORMATION: Targeting moiety

<400> SEQUENCE: 238

Phe Thr Cys Ser
1

<210> SEQ ID NO 239
<211> LENGTH: 4
<212> TYPE: PRT
<213> ORGANISM: Artificial Sequence
<220> FEATURE:
<223> OTHER INFORMATION: Targeting moiety

```
<400> SEQUENCE: 239

Phe Asn Cys Ser
1

<210> SEQ ID NO 240
<211> LENGTH: 4
<212> TYPE: PRT
<213> ORGANISM: Artificial Sequence
<220> FEATURE:
<223> OTHER INFORMATION: Targeting moiety

<400> SEQUENCE: 240

Phe Gln Cys Ser
1

<210> SEQ ID NO 241
<211> LENGTH: 4
<212> TYPE: PRT
<213> ORGANISM: Artificial Sequence
<220> FEATURE:
<223> OTHER INFORMATION: Targeting moiety

<400> SEQUENCE: 241

Phe Val Cys Ser
1

<210> SEQ ID NO 242
<211> LENGTH: 4
<212> TYPE: PRT
<213> ORGANISM: Artificial Sequence
<220> FEATURE:
<223> OTHER INFORMATION: Targeting moiety

<400> SEQUENCE: 242

Tyr Ser Cys Ser
1

<210> SEQ ID NO 243
<211> LENGTH: 4
<212> TYPE: PRT
<213> ORGANISM: Artificial Sequence
<220> FEATURE:
<223> OTHER INFORMATION: Targeting moiety

<400> SEQUENCE: 243

Tyr Thr Cys Ser
1

<210> SEQ ID NO 244
<211> LENGTH: 4
<212> TYPE: PRT
<213> ORGANISM: Artificial Sequence
<220> FEATURE:
<223> OTHER INFORMATION: Targeting moiety

<400> SEQUENCE: 244

Tyr Asn Cys Ser
1

<210> SEQ ID NO 245
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 245

Tyr Gln Cys Ser
1

<210> SEQ ID NO 246
<211> LENGTH: 4
<212> TYPE: PRT
<213> ORGANISM: Artificial Sequence
<220> FEATURE:
<223> OTHER INFORMATION: Targeting moiety

<400> SEQUENCE: 246

Tyr Val Cys Ser
1

<210> SEQ ID NO 247
<211> LENGTH: 4
<212> TYPE: PRT
<213> ORGANISM: Artificial Sequence
<220> FEATURE:
<223> OTHER INFORMATION: Targeting moiety

<400> SEQUENCE: 247

Trp Ser Cys Ser
1

<210> SEQ ID NO 248
<211> LENGTH: 4
<212> TYPE: PRT
<213> ORGANISM: Artificial Sequence
<220> FEATURE:
<223> OTHER INFORMATION: Targeting moiety

<400> SEQUENCE: 248

Trp Thr Cys Ser
1

<210> SEQ ID NO 249
<211> LENGTH: 4
<212> TYPE: PRT
<213> ORGANISM: Artificial Sequence
<220> FEATURE:
<223> OTHER INFORMATION: Targeting moiety

<400> SEQUENCE: 249

Trp Asn Cys Ser
1

<210> SEQ ID NO 250
<211> LENGTH: 4
<212> TYPE: PRT
<213> ORGANISM: Artificial Sequence
<220> FEATURE:
<223> OTHER INFORMATION: Targeting moiety

<400> SEQUENCE: 250

Trp Gln Cys Ser
1

<210> SEQ ID NO 251
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 251

Trp Val Cys Ser
1

<210> SEQ ID NO 252
<211> LENGTH: 4
<212> TYPE: PRT
<213> ORGANISM: Artificial Sequence
<220> FEATURE:
<223> OTHER INFORMATION: Targeting moiety

<400> SEQUENCE: 252

Met Gly Ala Gln
1

<210> SEQ ID NO 253
<211> LENGTH: 4
<212> TYPE: PRT
<213> ORGANISM: Artificial Sequence
<220> FEATURE:
<223> OTHER INFORMATION: Targeting moiety

<400> SEQUENCE: 253

Ala Gly Ala Gln
1

<210> SEQ ID NO 254
<211> LENGTH: 4
<212> TYPE: PRT
<213> ORGANISM: Artificial Sequence
<220> FEATURE:
<223> OTHER INFORMATION: Targeting moiety

<400> SEQUENCE: 254

Val Gly Ala Gln
1

<210> SEQ ID NO 255
<211> LENGTH: 4
<212> TYPE: PRT
<213> ORGANISM: Artificial Sequence
<220> FEATURE:
<223> OTHER INFORMATION: Targeting moiety

<400> SEQUENCE: 255

Ile Gly Ala Gln
1

<210> SEQ ID NO 256
<211> LENGTH: 4
<212> TYPE: PRT
<213> ORGANISM: Artificial Sequence
<220> FEATURE:
<223> OTHER INFORMATION: Targeting moiety

<400> SEQUENCE: 256

Leu Gly Ala Gln
1

<210> SEQ ID NO 257
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 257

Phe Gly Ala Gln
1

<210> SEQ ID NO 258
<211> LENGTH: 4
<212> TYPE: PRT
<213> ORGANISM: Artificial Sequence
<220> FEATURE:
<223> OTHER INFORMATION: Targeting moiety

<400> SEQUENCE: 258

Tyr Gly Ala Gln
1

<210> SEQ ID NO 259
<211> LENGTH: 4
<212> TYPE: PRT
<213> ORGANISM: Artificial Sequence
<220> FEATURE:
<223> OTHER INFORMATION: Targeting moiety

<400> SEQUENCE: 259

Trp Gly Ala Gln
1

<210> SEQ ID NO 260
<211> LENGTH: 4
<212> TYPE: PRT
<213> ORGANISM: Artificial Sequence
<220> FEATURE:
<223> OTHER INFORMATION: Targeting moiety

<400> SEQUENCE: 260

Ala Cys Ala Gln
1

<210> SEQ ID NO 261
<211> LENGTH: 4
<212> TYPE: PRT
<213> ORGANISM: Artificial Sequence
<220> FEATURE:
<223> OTHER INFORMATION: Targeting moiety

<400> SEQUENCE: 261

Val Cys Ala Gln
1

<210> SEQ ID NO 262
<211> LENGTH: 4
<212> TYPE: PRT
<213> ORGANISM: Artificial Sequence
<220> FEATURE:
<223> OTHER INFORMATION: Targeting moiety

<400> SEQUENCE: 262

Ile Cys Ala Gln
1

<210> SEQ ID NO 263
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 263

Leu Cys Ala Gln
1

<210> SEQ ID NO 264
<211> LENGTH: 4
<212> TYPE: PRT
<213> ORGANISM: Artificial Sequence
<220> FEATURE:
<223> OTHER INFORMATION: Targeting moiety

<400> SEQUENCE: 264

Met Cys Ala Gln
1

<210> SEQ ID NO 265
<211> LENGTH: 4
<212> TYPE: PRT
<213> ORGANISM: Artificial Sequence
<220> FEATURE:
<223> OTHER INFORMATION: Targeting moiety

<400> SEQUENCE: 265

Phe Cys Ala Gln
1

<210> SEQ ID NO 266
<211> LENGTH: 4
<212> TYPE: PRT
<213> ORGANISM: Artificial Sequence
<220> FEATURE:
<223> OTHER INFORMATION: Targeting moiety

<400> SEQUENCE: 266

Tyr Cys Ala Gln
1

<210> SEQ ID NO 267
<211> LENGTH: 4
<212> TYPE: PRT
<213> ORGANISM: Artificial Sequence
<220> FEATURE:
<223> OTHER INFORMATION: Targeting moiety

<400> SEQUENCE: 267

Trp Cys Ala Gln
1

<210> SEQ ID NO 268
<211> LENGTH: 4
<212> TYPE: PRT
<213> ORGANISM: Artificial Sequence
<220> FEATURE:
<223> OTHER INFORMATION: Targeting moiety

<400> SEQUENCE: 268

Ala Pro Ala Gln
1

<210> SEQ ID NO 269
<211> LENGTH: 4
<212> TYPE: PRT
<213> ORGANISM: Artificial Sequence
<220> FEATURE:
<223> OTHER INFORMATION: Targeting moiety
```

<400> SEQUENCE: 269

Val Pro Ala Gln
1

<210> SEQ ID NO 270
<211> LENGTH: 4
<212> TYPE: PRT
<213> ORGANISM: Artificial Sequence
<220> FEATURE:
<223> OTHER INFORMATION: Targeting moiety

<400> SEQUENCE: 270

Ile Pro Ala Gln
1

<210> SEQ ID NO 271
<211> LENGTH: 4
<212> TYPE: PRT
<213> ORGANISM: Artificial Sequence
<220> FEATURE:
<223> OTHER INFORMATION: Targeting moiety

<400> SEQUENCE: 271

Leu Pro Ala Gln
1

<210> SEQ ID NO 272
<211> LENGTH: 4
<212> TYPE: PRT
<213> ORGANISM: Artificial Sequence
<220> FEATURE:
<223> OTHER INFORMATION: Targeting moiety

<400> SEQUENCE: 272

Phe Pro Ala Gln
1

<210> SEQ ID NO 273
<211> LENGTH: 4
<212> TYPE: PRT
<213> ORGANISM: Artificial Sequence
<220> FEATURE:
<223> OTHER INFORMATION: Targeting moiety

<400> SEQUENCE: 273

Tyr Pro Ala Gln
1

<210> SEQ ID NO 274
<211> LENGTH: 4
<212> TYPE: PRT
<213> ORGANISM: Artificial Sequence
<220> FEATURE:
<223> OTHER INFORMATION: Targeting moiety

<400> SEQUENCE: 274

Trp Pro Ala Gln
1

<210> SEQ ID NO 275
<211> LENGTH: 4
<212> TYPE: PRT
<213> ORGANISM: Artificial Sequence
<220> FEATURE:
<223> OTHER INFORMATION: Targeting moiety

```
<400> SEQUENCE: 275

Ala Gly Val Gln
1

<210> SEQ ID NO 276
<211> LENGTH: 4
<212> TYPE: PRT
<213> ORGANISM: Artificial Sequence
<220> FEATURE:
<223> OTHER INFORMATION: Targeting moiety

<400> SEQUENCE: 276

Val Gly Val Gln
1

<210> SEQ ID NO 277
<211> LENGTH: 4
<212> TYPE: PRT
<213> ORGANISM: Artificial Sequence
<220> FEATURE:
<223> OTHER INFORMATION: Targeting moiety

<400> SEQUENCE: 277

Ile Gly Val Gln
1

<210> SEQ ID NO 278
<211> LENGTH: 4
<212> TYPE: PRT
<213> ORGANISM: Artificial Sequence
<220> FEATURE:
<223> OTHER INFORMATION: Targeting moiety

<400> SEQUENCE: 278

Leu Gly Val Gln
1

<210> SEQ ID NO 279
<211> LENGTH: 4
<212> TYPE: PRT
<213> ORGANISM: Artificial Sequence
<220> FEATURE:
<223> OTHER INFORMATION: Targeting moiety

<400> SEQUENCE: 279

Phe Gly Val Gln
1

<210> SEQ ID NO 280
<211> LENGTH: 4
<212> TYPE: PRT
<213> ORGANISM: Artificial Sequence
<220> FEATURE:
<223> OTHER INFORMATION: Targeting moiety

<400> SEQUENCE: 280

Tyr Gly Val Gln
1

<210> SEQ ID NO 281
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 281

Trp Gly Val Gln
1

<210> SEQ ID NO 282
<211> LENGTH: 4
<212> TYPE: PRT
<213> ORGANISM: Artificial Sequence
<220> FEATURE:
<223> OTHER INFORMATION: Targeting moiety

<400> SEQUENCE: 282

Ala Cys Val Gln
1

<210> SEQ ID NO 283
<211> LENGTH: 4
<212> TYPE: PRT
<213> ORGANISM: Artificial Sequence
<220> FEATURE:
<223> OTHER INFORMATION: Targeting moiety

<400> SEQUENCE: 283

Val Cys Val Gln
1

<210> SEQ ID NO 284
<211> LENGTH: 4
<212> TYPE: PRT
<213> ORGANISM: Artificial Sequence
<220> FEATURE:
<223> OTHER INFORMATION: Targeting moiety

<400> SEQUENCE: 284

Ile Cys Val Gln
1

<210> SEQ ID NO 285
<211> LENGTH: 4
<212> TYPE: PRT
<213> ORGANISM: Artificial Sequence
<220> FEATURE:
<223> OTHER INFORMATION: Targeting moiety

<400> SEQUENCE: 285

Leu Cys Val Gln
1

<210> SEQ ID NO 286
<211> LENGTH: 4
<212> TYPE: PRT
<213> ORGANISM: Artificial Sequence
<220> FEATURE:
<223> OTHER INFORMATION: Targeting moiety

<400> SEQUENCE: 286

Met Cys Val Gln
1

<210> SEQ ID NO 287
<211> LENGTH: 4
<212> TYPE: PRT
<213> ORGANISM: Artificial Sequence
<220> FEATURE:
<223> OTHER INFORMATION: Targeting moiety
```

```
<400> SEQUENCE: 287

Phe Cys Val Gln
1

<210> SEQ ID NO 288
<211> LENGTH: 4
<212> TYPE: PRT
<213> ORGANISM: Artificial Sequence
<220> FEATURE:
<223> OTHER INFORMATION: Targeting moiety

<400> SEQUENCE: 288

Tyr Cys Val Gln
1

<210> SEQ ID NO 289
<211> LENGTH: 4
<212> TYPE: PRT
<213> ORGANISM: Artificial Sequence
<220> FEATURE:
<223> OTHER INFORMATION: Targeting moiety

<400> SEQUENCE: 289

Trp Cys Val Gln
1

<210> SEQ ID NO 290
<211> LENGTH: 4
<212> TYPE: PRT
<213> ORGANISM: Artificial Sequence
<220> FEATURE:
<223> OTHER INFORMATION: Targeting moiety

<400> SEQUENCE: 290

Ala Pro Val Gln
1

<210> SEQ ID NO 291
<211> LENGTH: 4
<212> TYPE: PRT
<213> ORGANISM: Artificial Sequence
<220> FEATURE:
<223> OTHER INFORMATION: Targeting moiety

<400> SEQUENCE: 291

Val Pro Val Gln
1

<210> SEQ ID NO 292
<211> LENGTH: 4
<212> TYPE: PRT
<213> ORGANISM: Artificial Sequence
<220> FEATURE:
<223> OTHER INFORMATION: Targeting moiety

<400> SEQUENCE: 292

Ile Pro Val Gln
1
```

```
<210> SEQ ID NO 293
<211> LENGTH: 4
<212> TYPE: PRT
<213> ORGANISM: Artificial Sequence
<220> FEATURE:
<223> OTHER INFORMATION: Targeting moiety

<400> SEQUENCE: 293

Leu Pro Val Gln
1

<210> SEQ ID NO 294
<211> LENGTH: 4
<212> TYPE: PRT
<213> ORGANISM: Artificial Sequence
<220> FEATURE:
<223> OTHER INFORMATION: Targeting moiety

<400> SEQUENCE: 294

Phe Pro Val Gln
1

<210> SEQ ID NO 295
<211> LENGTH: 4
<212> TYPE: PRT
<213> ORGANISM: Artificial Sequence
<220> FEATURE:
<223> OTHER INFORMATION: Targeting moiety

<400> SEQUENCE: 295

Tyr Pro Val Gln
1

<210> SEQ ID NO 296
<211> LENGTH: 4
<212> TYPE: PRT
<213> ORGANISM: Artificial Sequence
<220> FEATURE:
<223> OTHER INFORMATION: Targeting moiety

<400> SEQUENCE: 296

Trp Pro Val Gln
1
```